US012011394B2

(12) United States Patent
Angelov et al.

(10) Patent No.: US 12,011,394 B2
(45) Date of Patent: Jun. 18, 2024

(54) DEVICES AND METHODS FOR LASER SURGERY OF AN EYE, ESPECIALLY FOR KERATOPLASTY

(71) Applicants: Carl Zeiss Meditec AG, Jena (DE); RESBIOMED TECHNOLOGIES OOD, Sofia (BG)

(72) Inventors: Alexander Angelov Angelov, Sofia (BG); Yavor Petrov Angelov, Sofia (BG); Mark Bischoff, Jena (DE); Robert Pomraenke, Jena (DE)

(73) Assignees: Carl Zeiss Meditec AG, Jena (DE); Resbiomed Technologies OOD, Sofia (BG)

( * ) Notice: Subject to any disclaimer, the term of this patent is extended or adjusted under 35 U.S.C. 154(b) by 200 days.

(21) Appl. No.: 17/602,874

(22) PCT Filed: Apr. 7, 2020

(86) PCT No.: PCT/EP2020/059869
§ 371 (c)(1),
(2) Date: Oct. 11, 2021

(87) PCT Pub. No.: WO2020/212199
PCT Pub. Date: Oct. 22, 2020

(65) Prior Publication Data
US 2022/0160547 A1 May 26, 2022

Related U.S. Application Data

(60) Provisional application No. 62/833,869, filed on Apr. 15, 2019.

(30) Foreign Application Priority Data

Apr. 1, 2020 (DE) .................. 10 2020 204 261.6

(51) Int. Cl.
*A61F 9/008* (2006.01)
*A61F 2/14* (2006.01)

(52) U.S. Cl.
CPC .......... *A61F 9/00831* (2013.01); *A61F 2/142* (2013.01); *A61F 9/00804* (2013.01);
(Continued)

(58) Field of Classification Search
CPC .. A61F 9/00831; A61F 2/142; A61F 9/00804; A61F 2009/00872; A61F 2009/00878; A61F 2009/00893
See application file for complete search history.

(56) References Cited

U.S. PATENT DOCUMENTS

| 5,789,240 A | 8/1998 | Abdulrazik |
| 2003/0014202 A1 | 1/2003 | Alexander et al. |

(Continued)

FOREIGN PATENT DOCUMENTS

| CN | 1043257 A | 6/1990 |
| DE | 10 2007 019815 A1 | 10/2008 |

(Continued)

OTHER PUBLICATIONS

International Search Report for PCT/EP2020/069869, dated Jul. 24, 2020, 6 pages.
Written Opinion of the ISA for PCT/EP2020/069869, dated Jul. 24, 2020, 12 pages.

*Primary Examiner* — Brian T Gedeon
*Assistant Examiner* — Joshua Andrew Schum-Houck
(74) *Attorney, Agent, or Firm* — DeWitt LLP

(57) ABSTRACT

Devices and methods of laser surgery of an eye, especially for refractive surgery, preferably for keratoplasty. The invention includes a planning and control unit, a system for laser surgery of an eye and a planning and control method wherein a device coordinate system of the first laser device and a device coordinate system of the characterization (Continued)

device are coupled using registration and measurement data or model data of the lamella can be unambiguously registered to the device coordinate systems, further by a defined edge geometry of the lamella, an ametropia correction during the generation of the lamella and by taking into account the hydration condition of the lamella, as well as methods for surgery.

21 Claims, 11 Drawing Sheets

(52) U.S. Cl.
CPC ........... *A61F 2009/00872* (2013.01); *A61F 2009/00878* (2013.01); *A61F 2009/00893* (2013.01)

(56) References Cited

U.S. PATENT DOCUMENTS

| | | | |
|---|---|---|---|
| 2009/0247999 A1* | 10/2009 | Tuan | A61B 90/98 606/5 |
| 2010/0069915 A1* | 3/2010 | Shiuey | A61F 2/147 606/107 |
| 2014/0264980 A1 | 9/2014 | Muller | |
| 2017/0027754 A1* | 2/2017 | Muller | A61F 9/00812 |
| 2018/0206482 A1 | 7/2018 | Zhang | |

FOREIGN PATENT DOCUMENTS

| | | |
|---|---|---|
| EP | 0289264 A1 | 11/1988 |
| EP | 1109007 A2 | 6/2001 |
| WO | WO 01/89373 A2 | 11/2001 |
| WO | WO 2008/131888 A1 | 11/2008 |
| WO | WO 2011/069516 A1 | 6/2011 |

\* cited by examiner

DEVICES AND METHODS FOR LASER SURGERY OF AN EYE, ESPECIALLY FOR KERATOPLASTY

RELATED APPLICATIONS

This application is a National Phase entry of PCT Application No. PCT/EP2019/059869 filed Apr. 7, 2020, which application claims the benefit of priority to U.S. Provisional Application No. 62/833,869 filed Apr. 15, 2019 and DE Application No. 10 2020 204 261.6 filed, Apr. 1, 2020, the entire disclosures of which are incorporated herein by reference.

TECHNICAL FIELD

Embodiments of the present invention relates to devices and methods for laser surgery of an eye, in particular for refractive surgery and for keratoplasty, especially to lamellar keratoplasty and, more particularly, but not exclusively, to Intrastromal Anterior Lamellar Keratoplasty, as for instance a sutureless Intrastromal Anterior Lamellar Keratoplasty (sIALK).

BACKGROUND

Diseases affecting the cornea are a major cause of blindness worldwide, second only to cataract in overall importance. The globally quantified shortage of corneal graft tissue shows 1 cornea available for 70 needed. Corneal disease affects 12.7 million individuals globally, and the current gold standard therapy using a human donor cornea (HDC) in low risk patients or keratoprosthesis in high risk patients is prone to graft rejection.

Devices and methods of refractive surgery, in particular for keratoplasty, as described for example in DE 10 2007 019 815 A1 and WO 2008/131888 A1, have so far assumed that a section of tissue is always removed from the recipient eye during treatment. Up to now, the sIALK procedure has been described in such a way that a resection is always necessary because only then a depression in the stromal bed (a so called "vacancy") would be created, which facilitates the correct positioning of an implant or transplant. A vacancy has inherent disadvantages, namely the surgical load and tissue loss associated with its creation. However, the advantages often outweigh the disadvantages: the extraction of biopsy material and the simplified positioning of the implant (or transplant).

In a special embodiment, in addition to an improvement in the corrected distance visual acuity (CDVA), uncorrected distance visual acuity (UDVA) is also improved. This means that an ametropia correction (in a way to also get rid of the use of the glasses, or at least to considerably improve ametropia) is carried out at the same time. This idea has already been formulated in parts in DE 10 2007 019 815 A1 and WO 2008/131888 A1.

Example embodiments of the invention include devices and methods for generating and implanting of a material resulting in a correction of a corneal geometry with improved precision. Embodiments of the invention facilitate the reconstitution of a normal corneal geometry with improved optical function of the cornea compared to prior art.

The invention includes different groups of measures or features, all of which serve the purpose of improving the above-mentioned devices and methods of refractive surgery, in particular for keratoplasty, and address different partial problems, but all of which ultimately serve the purpose of a common goal: to generate and implant a tissue or material for the purpose of correcting a corneal geometry with the highest and thus improved precision compared to the prior art.

With the optimized target geometry envisaged here by the described inventive devices and methods, the optical function of the cornea is improved. In particular, the correction achieved in this way makes it possible to restore an almost normal corneal geometry.

Each of the different groups of measures and features in itself leads to the desired improved precision in the production and implantation of a tissue or material for the purpose of correcting a corneal geometry. However, when these groups are combined, the benefits not only add up, but are reinforced in different ways, leading to further improved precision compared to a simple sum of the individual groups, as it will be explained at various occasions.

The first group concerns measures for an improved positioning of the vacancy. The first group further concerns a positionally correct implantation even without a vacancy. Instead of a vacancy a so-called pocket incision is used. Last but not least the first group concerns measures for centering and orientation as well as the order of steps.

The second group concerns measures for an improved shape of the implant (to avoid cavities), for an improved machining accuracy, and for the description of the shape of the implant itself.

The third group includes measures for an integrated refraction correction and for re-treatment (touch-up treatment).

The fourth group concerns measures for material improvement, especially the hydration state of the material.

Before describing these groups in detail, however, a few terms should be clarified:

"Implant" is a tissue or material of non-human origin.

"Transplant" is a tissue or material of human origin. (The distinction based on contained living cells may be relevant from a regulatory point of view but will be neglected here).

"Implantation" means the insertion of an implant or a transplant.

"Blank" means a blank which typically has a cylindrical round basic shape with a diameter of approx. 5 to 9 mm and a thickness of between 10 µm and 500 µm. The blank is processed to form a lamella.

Lamella" means an implant or transplant which is made from a blank and thus receives a thickness profile which is specially adapted to the recipient eye.

"Vacancy" refers to the structure in the stromal bed resulting from the resection (i.e. removal of a corneal volume). The vacancy can also be called a resection cavity, although it practically never really exists as a cavity in the cornea, but the lamella above it is always in contact with the stromal bed, and an initially created cavity is rapidly filled with tissue fluid.

As to the disadvantages of the prior art and the resulting problems to be solved, the following should be noted with regard to the first group of inventive measures:

In order to correctly position a vacancy or, as also suggested for the solution of the problem, to correctly position a pocket, a so-called SMILE operation is currently performed in the recipient eye with a minimal refractive correction (−0.75 dpt), During that SMILE operation, a lenticle is separated in the cornea of the recipient eye by use of a femtosecond laser (fs-laser) and then removed via a small incision. Correct centering is difficult in advanced keratoconus for three reasons:

The first problem is determining the correct centering target. Vertex centering is not necessarily unambiguous; therefore, one would rather center on the center of the pupil or limbus.

The second problem is to hit the centering target with a femtosecond laser device as well. A manual marking may help in this case. However, whether a fixation of the eye is done there on the right place depends on how the docking procedure is carried out, which is difficult to predict in the case of a deformed cornea (the condition in advanced keratoconus). Of course, the docking procedure can be repeated several times.

The third problem is that, up to now, it has been the user's responsibility to coordinate the centering of SMILE or pocket incision treatment and the centering of the lamella (or the lamella profile). This can result in considerable errors.

The generation of a certain orientation (angular feature e.g. position of the opening incision) is principally possible with various commercial femtosecond laser devices. Since most femtosecond laser devices considerably distort the cornea during fixation, a manual marking (e.g. with a marker pen) has to be done on the corneal surface. Only femtosecond laser devices with a curved contact lens (e.g. VisuMax) allow an angular alignment of the treatment in relation to the iris (or pupil) with sufficient accuracy. However, it is currently the user's responsibility to coordinate the angular orientation of a SMILE or pocket incision treatment and the angular orientation of the lamella (i.e. especially the lamella profile). This can result in considerable errors.

One way to achieve such a coordination is to use a so-called blank holder during the processing of the blank to produce the lamella. Since the processing profile for the blank on the holder is derived from the diagnostic data, there is, however, an uncertainty as to whether the profile orientation corresponds to the later eye orientation when the vacancy or the pocket is created.

If there is a deviation in the generation of the incisions in the recipient eye, this can only be compensated within certain limits, a problem that must therefore be solved in order to perform the correction of the corneal geometry with the highest precision and thus restore the normal corneal geometry with improved optical function of the cornea.

The considerations are therefore the following:

On the one hand, use of the vacancy is a way of improving the positional accuracy of the lamella. On the other hand, it must be ensured that the vacancy is correctly positioned. This is often problematic and requires improvement.

A second type is therefore proposed as a further variant of sIALK, in which the generation of a vacancy is not required. In contrast to the known variant, there is no resection incision and only a pocket is created which is large enough to accommodate the lamella and compensate for centering errors when creating the pocket. For this purpose, the lateral dimensions of the pocket are chosen to be at least 100 µm larger than those of the lamella. If the diameter is 100 µm larger, decentering of the pocket by up to about 50 µm can be compensated. However, this available range can be further limited if additional inaccuracies are encountered during the generation of the lamella, which is why the problem of adding inaccuracies has to be reduced, too.

In the event that the positioning of the vacancy is probably not successful, or even foreseeably not successful, the sIALK variant described here can be used: It does not generate a vacancy. In this case, the first step in the procedure in the recipient eye is to create a corneal pocket (incision), for which techniques are known. However, the correct position of the implantation becomes a more serious problem than in case of the creation of a vacancy.

When implanting a lamella, a lateral accuracy of profile adjustment is necessary. Conceivable here are about 10 µm to 50 µm, in any case not more than 200 µm. In addition, the angular orientation must be that precise that these dimensions are not significantly exceeded even in the periphery (radius 4 mm). This consideration leads to an angular accuracy of about 1° to 3°, which is another considerable practical problem. The currently practiced sequence of steps follows the principle of minimizing the treatment risk for the recipient eye by ensuring that the incisions in the recipient eye are made only after the preparation of the lamella (i.e. the implant or the transplant). If there is then a deviation during the creation of the incisions in the recipient eye, this can only be compensated within certain limits.

An example embodiment of the invention includes a planning unit for generating control data for a system for laser surgery of an eye, in particular for keratoplasty, comprising a first laser device and at least one characterization device,
  wherein the first laser device for generating at least one incision in a cornea, for example a femtosecond laser, is controllable by the control data, wherein the planning unit comprises:
  an interface for supplying first measurement data on corneal parameters from the characterization device, for example an OCT (optical coherence tomography) device,
  an interface for supplying second measurement data or model data of a lamella, insertable into the cornea after generation of the incision,
  an interface for transferring control data to the first laser device, and
  a computing circuity for determining the at least one incision in the cornea using the first measurement data and second measurement data or model data, wherein the computing circuity generates a control data set for controlling the first laser device, wherein the at least one incision can be generated by the first laser device using the control data set.

According to an example embodiment of the invention, a device coordinate system of the first laser device and a device coordinate system of the characterization device are coupled via the planning unit using registration and the supplied second measurement data or model data of the lamella can be unambiguously registered to the device coordinate systems via the planning unit.

In alternative embodiments of the planning unit, the incision to be generated in the cornea describes a pocket incision or the incision to be generated in the cornea comprises an anterior and a posterior surface such that it forms a corneal volume to be extracted.

In an example embodiment, the planning unit is further arranged for generating control data for a second laser device of the system for laser surgery of an eye for example an excimer laser, for processing a blank to the patient-specifically formed lamella. Therefor it is further comprising an interface for transferring control data to the second laser device. Further, a device coordinate system of the second laser device is also coupled using registration to the device coordinate system of the first laser device and the characterization device.

It is a matter of matching the centering of the SMILE or pocket incision and the centering of the lamella (the lamella profile). For this purpose, in particular a uniform corneal coordinate system is introduced by coupling the device coordinate systems by registration:

1. during the characterization of the cornea, for example by OCT measurement of the pachymetry map,
2. when planning the lamella position within the cornea,
3. when creating the vacancy or the pocket without a vacancy by use of the first laser device, for example a femtosecond laser device,
4. when processing the blank by use of the second laser device, for example an excimer laser device.

The processing of the blank, for example with an excimer laser device, is also carried out in such a way that the processing profile is "placed" exactly on the blank. This normally requires centering with an accuracy of about 100 µm. In that way it transforms the blank into a patient-specific lamella, whose implantation causes the intended regularization of the pachymetry and, if necessary, refraction adjustment.

The comprehensive planning of the operation is of great importance. For this purpose, a planning method, which is encoded in a planning software in the planning unit, is carried out using the planning unit. The measured corneal tomography data and, if necessary, other biometric parameters (e.g. radius of curvature, refraction) of the eye to be treated, are used as an input for the planning software. For this purpose, the planning unit, in which the planning software is encoded, can be an integral part of the system for laser surgery of an eye or can, in parallel or alternatively, be located on a computer which is physically separated from the system for laser surgery of an eye.

The user is shown the spatially resolved pachymetry of the patient's eye as well as at least one additional position marker (e.g. center of the photopic pupil, vertex position, limbus). In addition, the software provides information of the typical pachymetry map of a healthy eye. By positionally correct difference calculation of the existing pachymetry map with a typical pachymetry map, the software automatically determines a difference map. The user decides whether the procedure is to be performed with or without a vacancy, defines the treatment zone (usually round) by defining, for example, the lamella center and the lamella diameter, as well as other geometric parameters such as diameter and edge thickness of the vacancy, edge thickness of the lamella, depth of the pocket incision below the surface of the cornea. The software can also automatically suggest or set some or all of these parameters. Then, the software generates control data for the first laser device, for example a femtosecond laser device, as well as for the second laser device, for example the excimer laser device. These control data can and should include registration information, in particular:

1. the control data for a femtosecond laser device as a pre-processing second laser device for producing a blank in a source material, possibly in a donor eye. If the source material is already available in a suitable configuration, this step can be replaced by the data transfer concerning the geometry of the material.
2. the control data for an excimer laser device as a post-processing second laser device for processing the blank into a lamella.
3. the control data for the generation of a pocket incision or a vacancy in the recipient eye to receive the lamella.

The registration can be based, for example, on the position of the corneal vertex, the center of the pupil (especially for example the photopic pupil) or the position and orientation of the iris.

The lamella is provided with at least two distinguishable marks on its periphery. These are advantageously applied in such a way that flipping of the lamella can be detected by the user, for example at 0° and 90°. The marks can already be created with a femtosecond laser device as a second laser device, or more specifically, as the first of two second laser devices in use (such marks may be notches, noses, marking incisions on the surface or bubbles (incisions) inside the blank) and can be adapted for additional color marking.

An angle marking is also created during the pocket incision. It can be situated in the stromal bed or in the cap. In the simplest case, it can be a feature of the opening incision.

A further improvement in accuracy is achieved by the possibility of selecting the sequence of steps in the processing in such a way that the pocket incision or the resection is generated by the first laser device for example before processing the blank by the second laser device (for example by an excimer laser device). In this example embodiment of the invention, the pocket incision or the resection incision are thus generated before the blank is processed by application of the second laser device. Information about the position of the resection incision is then processed by the control software and the patient-specific shape of the lamella is then determined on the basis of the position of the resection incision (instead of vice versa), or it is corrected with respect to the original planning.

As to the disadvantages of the prior the art and the resulting problems to be solved, the following should be noted with regard to the second group of inventive measures:

Currently, there is no technology available to generate a defined edge geometry for a patient-specific shaped lamella. The femtosecond laser incisions used in the experimental procedure to create the cylindrical blank (actually a spherical shell) and the subsequent excimer laser processing to create a patient-specific lamella cannot yet produce a precise edge geometry. It can be assumed, for example, that the edge thickness alone randomly deviates from the target value by up to 30 µm or up to 100%.

The Zernike polynomials up to the 6th order used for patient-specific fitting by an excimer laser device as a second laser device represent a considerable limitation for the procedure. Although there is a 11th-order Zernike decomposition for a topographically guided treatment already existing in an excimer laser device, such as the MEL, this treatment method has not yet been applied ex-vivo and is not accessible so far for the procedure practiced here. Therefore, there is currently no other proven technology for controlling an excimer laser device during the ex-vivo processing of a lamella.

Currently, sIALK uses a lamella with an edge thickness of at least 30 µm. This makes sense with regard to the mechanical strength and manipulability of the lamella, but despite the vacancy it leads to the formation of an annular cavity at the point of contact between the stroma, lamella and cap. Although a cavity like that fills with tissue fluid, it is unphysiological and should be avoided if possible. Therefore, there is no prior art technology to create a special edge geometry of the lamella.

A precise geometry is difficult to produce with an excimer laser device if the spatial frequencies are high compared to the beam diameter. The production of a simple cylindrical blank with a femtosecond laser device already shows that with a femtosecond laser device it is basically possible to produce precise edges. For this reason, a combination of processing steps with a femtosecond laser device as a pre-processing second laser device and an excimer laser device as a post-processing second laser device is proposed, but further processing principles have to be respected as described here below.

A further problem is to adequately describe the processing from the generation of the blank to the finished lamella for the laser devices. Especially the Zernike polynomial representation (wavefront representation) of the excimer laser processing used so far is problematic.

A further advantageous example planning unit is arranged for generating control data for the second laser device such that a defined edge geometry is achieved in the patient-specifically formed lamella, wherein in the case of a pocket incision, and thus without creating a vacancy, the edge thickness is a maximum of 30 µm, for example between 5 µm and 15 µm, or in the case of an extracted corneal volume, and thus with creation of a vacancy, the edge thickness of the lamella is adapted to the geometry of the vacancy.

It is of further advantage for example, if the planning unit is arranged for determining a substantially annular transition zone at the edge of the lamella within which the edge thickness gradually changes into a patient-specific thickness profile, and control data is generated such that it prevents from processing of the edge of the lamella by the second laser device.

The edge of the lamella should therefore essentially already be created during the generation of the blank by application of a femtosecond laser device as a pre-processing second laser device according to the specifications, while the actual processing/individualization of the lamella before the implantation in a recipient eye is carried out by application of an excimer laser device as a post-processing second laser device.

A further example planning unit is arranged for generating control data for a temperature regime for maintaining a temperature below a maximum temperature for processing the lamella with the second laser device.

These measures to a defined edge of the lamella and a defined temperature regime are particularly effective if the device coordinate systems of the first laser device, the characterization device and the second laser device are coupled by registration in the planning unit, and the supplied second measurement data or model data of the lamella can be unambiguously registered to the device coordinate systems. But even without such coupling and registration to each other, the measures for a defined edge of the lamella and a temperature regime during processing contribute to an improved precision compared to the prior art and in particular to a restoration of a normal corneal geometry with an improved optical function of the cornea compared to prior art.

The creation of a defined edge geometry in a patient-specific shaped lamella is achieved by adapting the target thickness of the edge to the vacancy geometry. If no vacancy is created at all, the edge thickness is a maximum of 30 µm, but for example only 5 to 15 µm. In a special embodiment of the invention, the edge thickness is exactly adapted to the vacancy when a vacancy is created. The edge thickness is the thickness of the outermost 10 µm annular zone at the edge of the lamella.

In addition, an annular transition zone is provided at the edge with a radial width of at least 10 µm, for example with a radial width of between 50 µm and 500 µm. Within this transition zone, the edge thickness is gradually converted to the patient-specific thickness profile. In the simplest case this is done by a linear transition from the edge thickness D(r=r_max, Phi) to D(r=r_max−edge width, Phi). Further configurations are obvious for the expert, smoothing in Phi is also possible.

The edge thickness and the profile within the transition zone is achieved by the interaction of a femtosecond laser device as a pre-processing second laser device and an excimer laser device as a post-processing second laser device. In particular, in one aspect, the excimer processing is performed in such a way that no excimer ablation occurs on the edge of the blank. This is because, on the one hand, it should be prevented that the edge thickness precisely produced with the femtosecond laser device is changed by the excimer laser device and, on the other hand, no ablation of the blank carrier—the cornea holder—should occur because this could contaminate the lamella. In order to further improve this aspect, in variant of the invention, the transition zone is wholly or partially created by the femtosecond laser device as a pre-processing second laser device, for example by creating a conical basic geometry of the edge zone of the blank.

The control of an excimer laser device during the ex-vivo processing of a lamella is currently performed with a shot pattern that breaks down the Zernike development of the difference profile into individual ablation volumes. Currently, this development is only performed up to the 6th order of the polynomial. However, development beyond the 6th order is useful for these ex-vivo operations in order to be able to create more refined structures. However, it is not absolutely necessary to carry out such a development. Instead, the difference profile can be broken down directly into individual ablation volumes (shot decomposition). In any case, it is essential to perform the processing in such a way that the temperature of the blank does not exceed 40° C. For this purpose, the shot distribution and laser frequency of the scanning-spot-laser are adjusted accordingly.

In an aspect of the invention, the blank is actively cooled before and/or during processing with the excimer laser device. In a special aspect of the invention the cooling is below 10° C. In another aspect of the invention, the cooling is below the freezing point of the blank. The waste products of the processing are actively removed by application of controlled air flow. Again, in an aspect of the invention, the air flow is actively controlled with respect to temperature and/or humidity. In another aspect of the invention, a technical gas (e.g. nitrogen) is used instead of air. In another aspect of the invention, the processing is monitored continuously or cyclically. Monitored parameters are for example surface temperature, removal volume, material thickness, surface topography, axial and lateral position of the blank. In a further aspect of the invention, the monitored parameters are used to control the removal process.

As to the disadvantages of the prior art and the resulting problems to be solved, the following should be noted with regard to the third group of inventive measures:

The improvement in visual acuity (CDVA) associated with regularization of corneal thickness is already a good result for the patient. In principle, in order to achieve good uncorrected visual acuity (UCVA), there is also the possibility of performing refractive correction treatment, but a photorefractive keratectomy (PRK) would always be associated with the loss of the Bowman membrane, which is a medically questionable option in a biomechanically unstable eye. Laser in-situ keratomileusis (LASIK) is prohibited due to the even greater biomechanical implication and femtosecond lenticular extraction (Small Incision Lenticle Extraction, SMILE) treatment would hardly be surgically feasible. An anterior chamber lens would be conceivable, but it is a high risk for such a patient. The same applies to an intraocular lens (IOL), which in this case would replace a non-opaque lens (clear lens exchange).

As long as only the regularization of the corneal thickness (pachymetry) is attempted, a condition is achieved in which the patient's eye has good visual acuity by the use of a visual aid (glasses, contact lenses). If an even better visual acuity condition is targeted, for example, that good visual acuity can be achieved without correction of glasses, this requires additional measures. The basic principles for solving this problem have already been formulated in parts in DE 10 2007 019 815 A1 and WO 2008/131888 A1, but no concrete or even advantageous embodiments are known to date.

It is to be expected that a refraction correction in a keratoconus diseased eye during a keratoplasty treatment will only be possible up to a certain degree, because biomechanical assumptions have to be made which are on the one hand inaccurate due to individual biomechanical properties of the eye, and on the other hand a biomechanical change of the recipient eye can and should be caused by the transplantation itself. Depending on the individual case, this may be associated with a change in shape, which then requires a possibility for subsequent correction.

A further advantageous example planning unit is arranged for generating control data for a second laser device such that an ametropia correction is achieved.

To become concrete, an especially advantageous example is a planning unit, which is arranged for generating control data for the second laser device such that a refractive power and/or an astigmatism is applied to the blank.

Of special interest is an example planning unit, which is arranged for generating control data for a subsequent correction by replacing the inserted lamella by a corrected lamella, taking into account stored control data of the inserted lamella.

Data archiving, especially on all processing and characterization data of an inserted lamella, is therefore an advantageous example embodiment, and the planning unit has advantageously for example access to that data archiving via appropriate interfaces.

These measures for simultaneous refractive correction and in particular for a re-treatment (touch-up treatment) of the refractive correction are particularly effective if the device coordinate systems of the first laser device, the characterization device and if applicable the second laser device are coupled via the planning unit by registration and the supplied second measurement data of the lamella can be unambiguously registered to the device coordinate systems as well by the planning unit: It improves the result of this refractive correction quite considerably. However, even without such coupling and registration to each other, the measures for simultaneous refractive correction and in particular for a re-treatment of the refractive correction contribute to an improved precision compared to the prior art and in particular to a restoration of a normal corneal geometry with an improved optical function of the cornea.

The integration of a refractive correction to correct ametropia of a recipient's eye in the sIALK method represents a challenge in various ways. In one example variant of the invention, this refractive correction is achieved by adapting the control data of the excimer laser unit as a post-treatment second laser unit. In a second variant of the invention, this is done by adapting the control data for the femtosecond laser device as a pre-processing second laser device for the generation of the blank and the removal of the lamella to be implanted from this blank. For this second example variant, a blank of constant thickness is not generated anymore, nor an existing refractive power is subsequently completely compensated for by excimer laser processing. Instead, a refractive power is intentionally applied to the blank. The technological principles to do so are known from the SMILE procedure. A spherical refractive power between −20 and +20 dpt and/or an astigmatism between −10 and +10 dpt may for example be obtained. A refractive power of 0 dpt in the recipient's eye (apart from the higher order refractive power) is also explicitly possible and requires an inhomogeneous thickness of the blank. In this way, the processing is separated into a part that describes the change in refractive power induced by the lamella in the recipient's eye and a part that serves exclusively to correct irregular pachymetry and is shaped by the excimer laser device. It is possible to adapt the incision by the femtosecond laser device in the blank for that reason in an anterior and/or posterior incision into the blank.

In further aspects of the invention, the planning software has the ability to predict the postoperative radius of curvature of the cornea (cornea) or the spatially resolved curvature or topography of the postoperative cornea. It can also calculate the postoperative refractive power and, in combination with other biometric parameters of the recipient eye, predict the refraction of the recipient eye after implantation. In a continuation of the invention, the planning software can use a target refraction of the recipient eye entered by the user to adjust the implant (or transplant) accordingly. In the simplest case, the following procedure is carried out:

1. calculating a lamellar profile (profile=2D-map) as a difference profile between ideal pachymetry and existing pachymetry of the recipient eye;
2. prognosis of the post-operative refractive power of the cornea of the recipient eye by adding the lamella profile to the existing corneal profile;
3. calculating the refractive power of the recipient eye based on biometric parameters (e.g. axial length, lens refractive power, refraction, etc.) and predicted postoperative refractive power of the cornea;
4. calculating the difference between the predicted refractive power (S, C) of the recipient eye with the target refraction desired by the user;
5. if the difference is higher than a defined tolerance limit: changing the lamella profile by a corresponding lenticular tissue volume, e.g. additive, and repeating the procedure from step 2;
6. calculating the blank profile as a refraction-neutral lamella profile with the maximum thickness of the lamella profile to be generated;
7. calculating the ablation profile for ex-vivo processing of the blank with an excimer laser device as a second laser device;
8. generating the control data for the excimer laser device as a post-processing second laser device from the ablation profile (shot decomposition) and the control data for the femtosecond laser device as a pre-processing second laser device and as a first laser device (i.e., the incision for blank generation and the incision for pocket generation).

A further developed embodiment of the procedure provides inclusion of biomechanical aspects in the prognosis of the post-operative situation of the recipient eye. Thus, therapeutic effects can be considered as well as the effect of more complex add-on structures of the lamella, for example a ring-shaped thickening of the periphery.

Another further developed embodiment includes spherical aberration in addition to S and C in the prognosis and optimization.

The pocket incision with the first laser device is for example generated at a depth of 100 to 300 μm below the surface of the cornea.

If the implantation of the lamella has not led to a satisfactory UCVA, there is the possibility to perform a follow-up correction (re-treatment, touch-up) by replacing the implant with a corrected implant. This is simplified by the fact that the planning software for planning the operation generates and saves a protocol of the lamella geometry. If necessary, this can be used later to create a corrected lamella. For this purpose, the patient's existing refraction is used and the original (archived) lamella geometry is adjusted accordingly. The resulting correction profile usually has a slightly larger volume than the original correction profile. The larger the diameter of the correction zone, the higher the difference between the correction profile and the original profile. However, the difference volume is less than 4 $\mu m^3$/dpt, for example less than 2 $\mu m^3$/dpt, when correcting residual myopia.

As to the disadvantages of the prior art and the resulting problems to be solved, the following should be noted with regard to the fourth group of inventive measures:

The problem of different hydration is already known in corneal transplantation and is reduced by specific treatment of the transplants. In conjunction with sIALK, however, it occurs for the first time in that extent, because corneas have not been shaped yet ex-vivo, e.g. with an excimer laser device, to match the patient's specific needs. In addition to swelling and shrinking, the ablation efficiency of the excimer laser device is altered by hydration.

By analyzing the previous procedure, it became apparent that the variability of the material, especially its hydration state, can be the source of considerable errors. This was not clear until now and requires appropriate measures to ultimately be able to predict more precisely the geometry of the lamella in the recipient cornea, especially its thickness.

Another example planning unit is arranged for generating control data taking into account a defined initial hydration condition of the blank (transplant or implant) or the lamella ex-vivo and the change in the hydration condition of the lamella during or after implantation, for example by using a constant expansion factor, or a first factor for thickness expansion and a second factor for lateral expansion.

This measure for a defined initial hydration state and the consideration of the change of the hydration state of the blank or the lamella is particularly effective if the device coordinate systems of the first laser device, the characterization device and, if applicable, the second laser device are coupled in the planning unit by registration and the supplied second measurement data of the lamella can be unambiguously registered to the device coordinate systems by the planning unit. But even without such coupling and registration to each other, the measures for a defined initial hydration state and the consideration of the change of the hydration state during processing contribute to an improved precision compared to prior art and in particular to a restoration of a normal corneal geometry with an improved optical function of the cornea.

The problem of different hydration leads to swelling and shrinking of the blank or lamella. In addition, the hydration changes the ablation efficiency, especially of an excimer laser device. This problem is solved by bringing the starting material into a defined state. According to the invention, it is of secondary importance which state is reached as long as a constant expansion factor between the ex-vivo state of the blank and the implanted state of the later lamella exists for the thickness E, which is determined and used to calculate the control data for the processing of the blank. E can therefore be greater than 1 (increase in lamella thickness after implantation) or less than 1 (decrease in lamella thickness after implantation), but it is advisable not to deviate too much from 1: This keeps possible errors small, and lateral expansion, which does not necessarily occur with the same factor, is also small. This lateral expansion is also used in a further variant of the invention to calculate the control data.

The blank or lamella can also be dyed with a dye for better handling, which gradually disappears after the lamella has been implanted.

An additional possibility for improved control of the hydration state is the use of an artificial material (e.g. bio-engineered material) with well-defined parameters, from which the lamella to be implanted can then be worked out in a more controlled manner using the second laser device—as a replacement for a natural transplant material.

The problem is further solved by a control unit of a system for laser surgery of an eye, comprising:
- a memory comprising a treatment program, wherein said treatment program comprises a program for refractive correction and for dissecting and/or ablating a cornea to have a treatment zone having a maximal dimension in a range between 8 mm and a maximal dimension maximal value of the cornea;
- a control circuitry configured to signal a laser device to dissect and/or ablate a cornea according to said treatment program.

The control unit is thus taking up the control data defined by the planning unit to process the treatment program.

Furthermore, the problem is also solved by a system for laser surgery of an eye, comprising:
- a femtosecond laser;
- an excimer laser;
- a memory comprising a treatment program, wherein said treatment program comprises a program for refractive correction and for dissecting and/or ablating a cornea to have a treatment zone having a maximal dimension in a range between 8 mm and a maximal dimension maximal value of the cornea;
- a control circuitry configured to signal said femtosecond laser and said excimer laser to dissect and ablate a cornea according to said treatment program.

As to said memory of the system for laser surgery of an eye, this system comprises at least one memory, but may also comprise several memories which are physically separated from each other.

In a example embodiment, the control circuitry of the system for laser surgery of an eye comprises a first control circuitry configured to signal said femtosecond laser and a second circuitry configured to signal said excimer laser to dissect and ablate a cornea according to said treatment program.

The problem is further solved by a system for laser surgery of an eye, in particular for keratoplasty, comprising a first laser device, for example a second laser device, and at least one characterization device, and an above described planning unit.

In a example embodiment, the system for laser surgery further comprises the above described control unit, the treatment program for example using the control data generated by the above described planning unit.

The problem is also solved by a cornea holder, comprising: an elongated base having a longitudinal axis and an upper curved surface along at least 50% of the surface area, wherein said curved surface is shaped and sized to hold at least a portion of a cornea in a curved orientation.

In an example embodiment of the cornea holder, said curved surface has a radius of curvature in a range of 7 to 9 mm along the entire curved surface.

A further example embodiment of the cornea holder is comprising an alignment portion located at or adjacent to said upper curved surface, wherein said alignment portion comprises one or more alignment markings shaped and sized to align said upper curved surface with alignment markings or a coordinate system of a laser surgical device.

Especially is a cornea holder for example, wherein said alignment portion comprises one or more rotation orientation markings shaped and sized to be positioned near at least a portion of a cornea, wherein said rotation orientation marking are configured to allow marking of the cornea by forming a cut or a void in the cornea to set a rotation orientation of the cornea with respect to said rotation orientation marking of said holder.

In a further advantageous example cornea holder, said one or more rotation orientation markings comprise an opening or an indentation in said alignment portion.

The problem is also solved by a method for planning realizing the generation of control data for a system for laser surgery of an eye, for example for keratoplasty, comprising a first laser device, for example a second laser device, and at least one characterization device, and a planning unit, according to an encoding of the above described planning unit.

A whole series of methods may be planned by the above described planning unit, using for this purpose the described planning method, which is encoded in a planning software in the planning unit, the generated control data being run via a control unit on an above described system for laser surgery of an eye:

A method for reshaping a cornea, comprising:
placing a cornea on a cornea holder;
dissecting said cornea to define boundaries of a cornea portion while said cornea is placed in said cornea holder;
geometrically reshaping an outline of an external surface of said cornea portion while said cornea portion is placed in said cornea holder and is not separated from the cornea in said cornea holder.

In an embodiment of the method for reshaping a cornea, said cornea comprises an in-vitro formed cornea implant, an animal cornea, a human donor cornea lenticule or a human donor cornea.

In a further embodiment of the method for reshaping a cornea, said dissecting comprises dissecting said cornea to define a cornea portion after said dissecting having a maximal dimension of at least 7 mm.

A method for replacing a portion of a cornea, comprising:
calculating a size of a cornea portion to be removed from a cornea;
removing said cornea portion to form an implantation site while keeping an upper layer of the cornea intact;
implanting a cornea implant having a diameter which is smaller in at least 50 µm from a diameter of the implantation site into the implantation site and under the intact upper layer.

An embodiment of the method for replacing a portion of a cornea comprises:
calculating a size of a cornea portion to be removed from a cornea;
removing said cornea portion to form a structure to lock in an implant while keeping an upper layer of the cornea intact;
implanting a cornea implant having a counter-structure to lock in into the implantation site under the intact upper layer.

A further embodiment of the method for replacing a portion of a cornea comprises performing a Small Incision Lenticule Extraction (SMILE) laser surgery step prior to said removing.

A further embodiment of the method for replacing a portion of a cornea, comprising performing a Small Incision Lenticule Extraction (SMILE) surgery prior to said removing with abnormal attempted refractive power change of less than 0.75 dpt or even less than 0.25 dpt.

A further embodiment of the method for replacing a portion of a cornea comprises dissecting said cornea by a surgical laser device based on said calculated size.

In a further embodiment of the method for replacing a portion of a cornea, said calculating comprises calculating thickness values of said cornea portion to be removed at one or more locations along an area of said cornea portion, and said dissecting comprises ablating said cornea according to said calculated thickness values.

A method for forming a treatment zone in a cornea, comprising:
activating one or more lasers to apply laser beams on a cornea in a subject, wherein said laser beams are configured to dissect and/or ablate said cornea;
forming a treatment zone having a maximal dimension larger than 8 mm but smaller than a maximal dimension of said cornea, in said cornea by said laser beams configured to dissect and/or ablate said cornea.

In a further embodiment of the method for forming a treatment zone in a cornea, said one or more lasers comprise a femtosecond laser and/or an excimer laser.

A further embodiment of the method for forming a treatment zone in a cornea comprises removing tissue from said treatment zone in said cornea through an incision formed at a periphery of the cornea at a distance larger than 4 mm from a center of the cornea.

In a further embodiment of the method for forming a treatment zone in a cornea said incision extends in a circumferential direction and is smaller from a maximal dimension of a cornea implant.

A method for removal of a damaged tissue region from the cornea, comprising:
identifying a damaged region in the cornea;
calculating dimensions of at least a portion of said damaged region selected to be removed from the cornea;
removing said selected damaged portion from the cornea.

A further embodiment of the method for removal of a damaged tissue region from the cornea comprises:
analyzing the cornea using optical coherence tomography (OCT), and wherein said calculating comprises calculated said dimensions based on said analysis results.

In a further embodiment of the method for removal of a damaged tissue region from the cornea said calculating comprises calculating size and/or shape of a cornea implant to be inserted into said cornea instead of said removed damaged region.

A method for implanting a material into a cornea, comprising:
calculating a pocket incision inside a cornea;
the pocket incision having lateral dimensions and an incision;

implanting a cornea implant having lateral dimension which are smaller than the lateral dimensions of the pocket incision under the intact upper layer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module", "unit", "device" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an embodiment of the invention, one or more tasks according to some embodiments of methods and/or systems as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create applications for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer and may not be feasible or practical for performing purely manually, by a human expert. A human expert who wanted to manually perform similar tasks, such as define freeform surface matrix and/or other characteristics of an implant, might be expected to use completely different methods, e.g., making use of expert knowledge and/or the pattern recognition capabilities of the human brain, which would be vastly more efficient than manually going through the steps of the methods described herein.

The object, features and advantages of the present invention and its modes of operation as well as advantageous combinations of different features will become more apparent considering the following detailed description and embodiments with reference to the accompanying drawings.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION

Figure 1A:
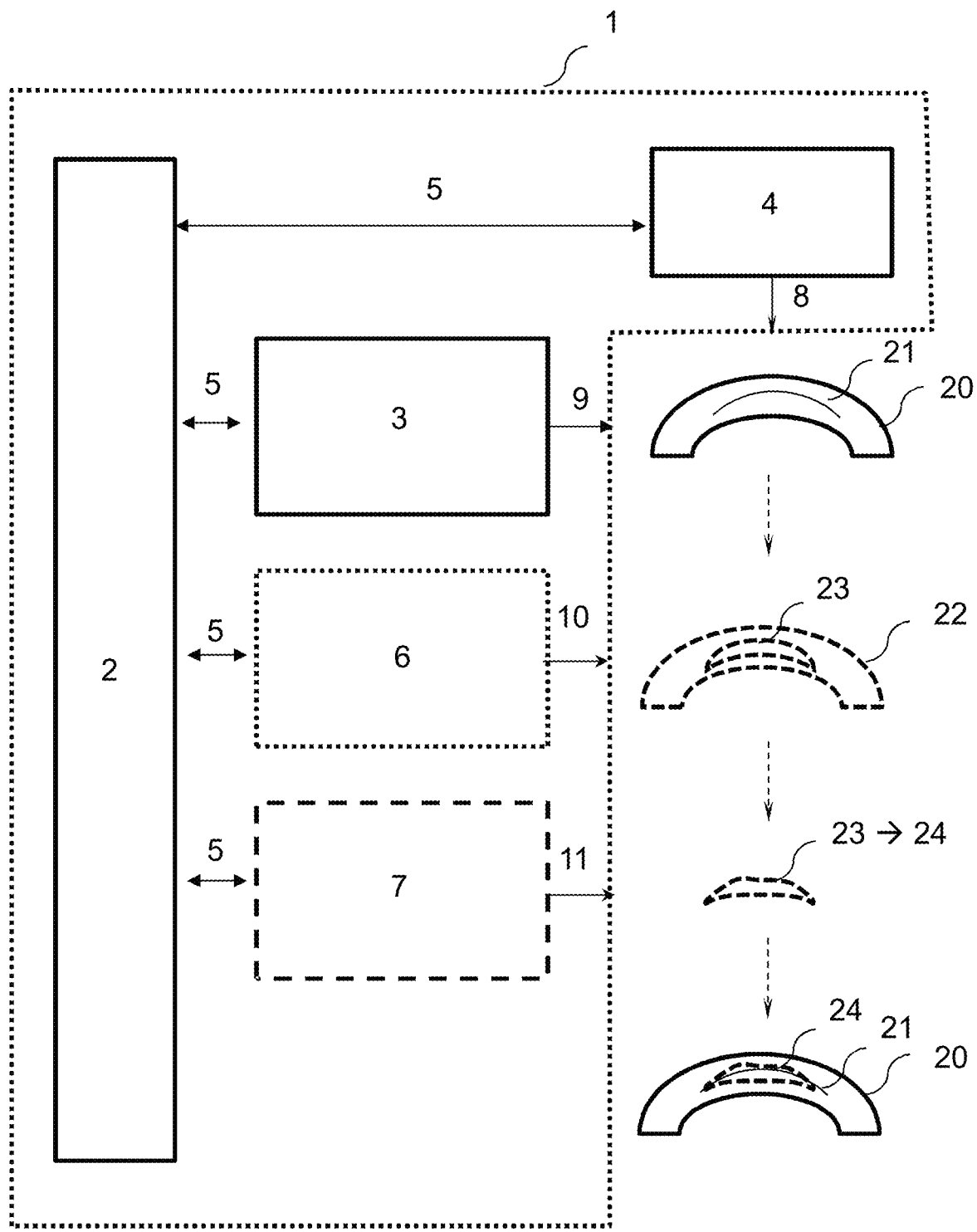
FIG. 1a is a scheme of a first system for laser surgery of an eye with a first planning unit according to an example embodiment of the invention, which does not reflect the exact physical conditions.
Figure 1B:
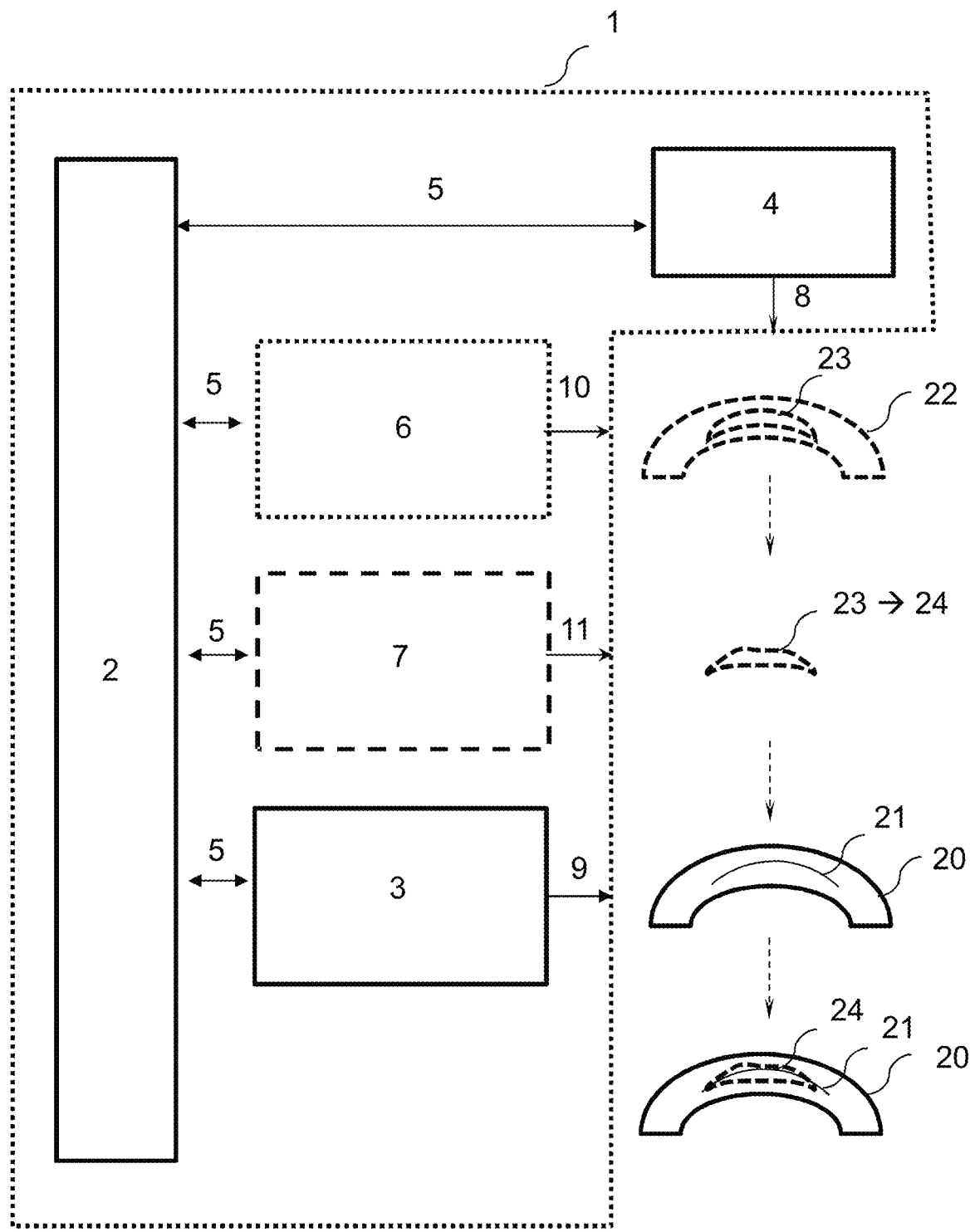
FIG. 1b is a scheme of a second system for laser surgery of an eye with a second planning unit according to an example embodiment of the invention.
Figure 1C:
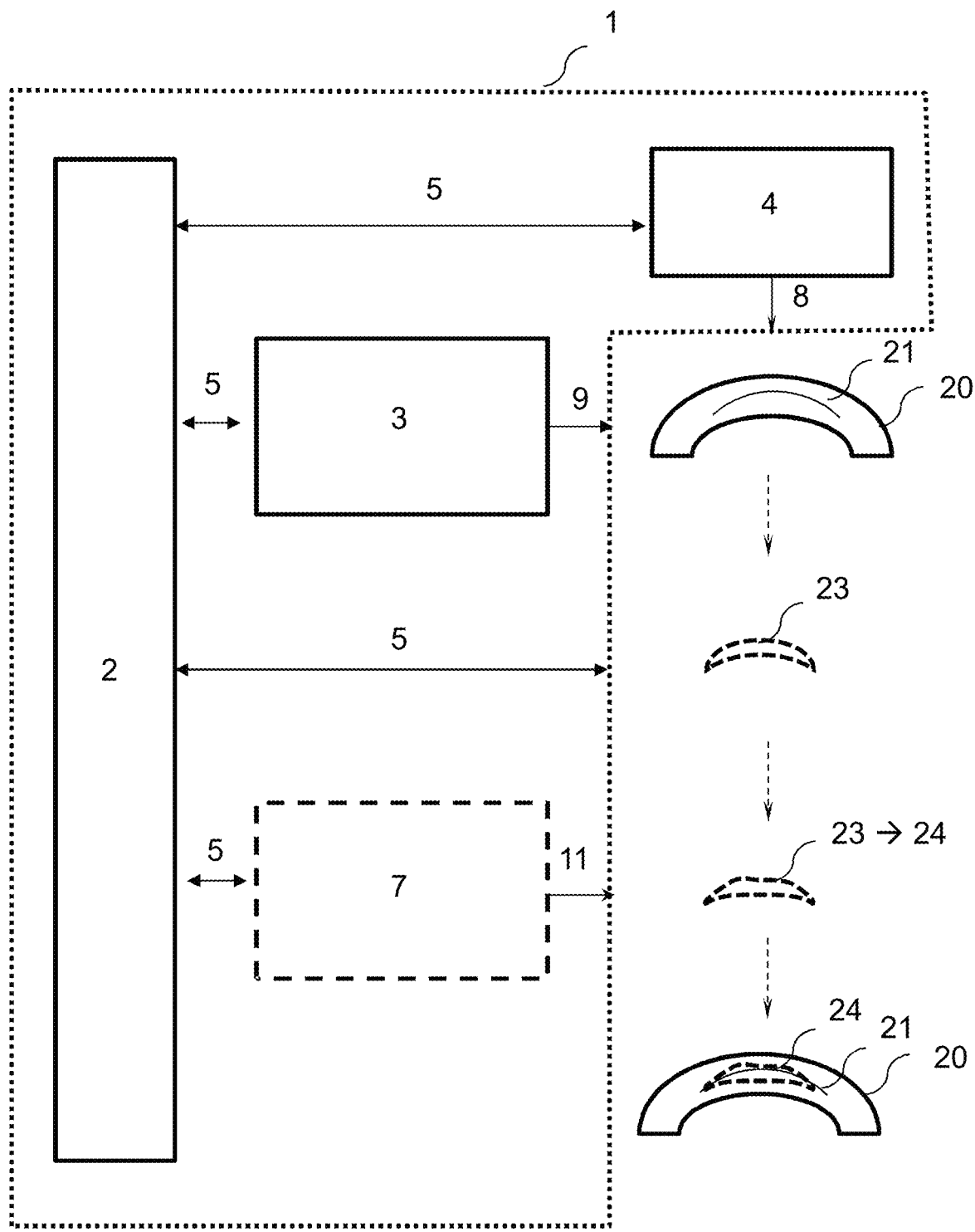
FIG. 1c the scheme of a third system for laser surgery of an eye with a third planning unit according to an example embodiment of the invention.

In all FIGS. 1a to 1c, the system 1 for laser surgery of an eye comprises a planning unit 2, a characterization device 4, which is set up to generate measurement data on parameters of the cornea of an eye with an characterization radiation 8, a first laser device 3, which here is a femtosecond laser device and which is arranged to generate a vacancy or, as shown here, a pocket incision 21 in the cornea of a recipient eye 20 by application of a focused femtosecond laser beam 9 (the direction of incidence of the beam is not shown here—one skilled in the art is aware of the optical design of such devices). All characterization and laser devices of the system 1 for laser surgery of an eye comprises interfaces 5 to the planning unit 2.

FIGS. 1a and 1b further comprise a pre-processing second laser device 6, which is also a femtosecond laser device, whereby the first femtosecond laser device 3 and the pre-processing second femtosecond laser device 6 can be one and the same device or two different laser devices. The pre-processing second laser device cuts a blank 23 from the cornea of a donor eye 22 with a focused femtosecond laser beam 10. FIGS. 1a to 1c further comprise a post-processing excimer laser device 7, which processes the lamella 24 to be implanted out of the blank 23 with an excimer laser beam 11, the lamella 24 finally being implanted into the pocket incision 21 in the cornea of the recipient eye 20.

The planning unit 2 is arranged to couple the device coordinate systems of the involved laser devices 3, 6, 7 and characterization devices 4 by registration and to also unambiguously register the supplied measurement data or model data of the lamella 23 to be implanted to the device coordinate systems.

While in FIG. 1a the pocket incision 21 is made first in the cornea of the recipient eye 20, and only afterwards the blank 23 is created in the donor eye and removed from it in order to process it into the lamella 24, in FIG. 1b first the blank 23 is completely processed into the lamella 24 to be implanted. Only subsequently, a pocket incision 21 is made in the cornea of the recipient eye 20 to prepare for the implantation of the lamella 24.

In FIG. 1c, on the other hand, a standardized blank 23 is used, which is then processed into the lamella 24.

The present invention, in some embodiments thereof, relates to Lamellar Keratoplasty and, more particularly, but not exclusively, to Intrastromal Anterior Lamellar Keratoplasty.

An aspect of some embodiments relates to in-vitro reshaping, for example geometrical reshaping, a cornea, for example an in-vitro formed implant or a human donor cornea (HDC) lenticule. In some embodiments, the cornea implant is reshaped prior to implantation in a recipient cornea in-vivo. In some embodiments, the cornea implant is reshaped according to one or more of structural, anatomical or clinical parameters of the recipient cornea. Alternatively or additionally, the cornea implant is reshaped to fit a void, also called "vacancy", formed in the recipient cornea.

According to some example embodiments, reshaping of the cornea implant, for example geometrical reshaping, means reshaping of an external surface of the cornea that following implantation faces the external environment. In some embodiments, reshaping comprises modifying a thickness of the cornea implant, for example by removing tissue from the external surface of the cornea implant at one or more geometrical locations located on the external surface. Additionally, the reshaping is performed in an x-y-z coordinates system, having a reshaping range, in an x-y axis plane, which is larger than a reshaping range in a z-axis direction.

According to some embodiments, the cornea implant is dissected, for example cut while placed in a cornea holder. In some embodiments, the cornea implant is cut, for example to set boundaries of a cornea portion, for example a cornea lenticule, from the cornea implant, while the cornea implant is placed in the cornea holder. Optionally, the cornea implant is cut on the cornea holder using a femtosecond laser. In some embodiments, after cutting, the cornea portion is not separated from the rest of the cornea implant or from the cornea.

According to some example embodiments, the cornea implant or the cornea portion is geometrically reshaped while placed in the cornea holder. In some embodiments, geometrically reshaping comprises reshaping of an outline of an external surface of the cornea implant or the cornea portion. In some embodiments, the geometrically reshaping is performed before, during or after the cutting.

An aspect of some embodiments relates to replacing a portion of a cornea, for example a human cornea or an animal cornea, with a cornea implant. In some embodiments, the replaced portion is an internal portion of the cornea. In some embodiments, the cornea implant comprises an in-vitro formed implant or a human donor cornea (HDC) lenticle implant. In some embodiments, the cornea implant shape, boundaries and/or size are adjusted according to the shape, boundaries and/or size of the replaced cornea portion. Optionally, a flap is not formed in the recipient eye for implantation of the cornea implant. As used herein, a flap is a layer of the eye that can be folded back to expose a working area that has a difference in area size of less than 30% compared to the area size of the folded layer covering the working area. In some embodiments, the portion of the cornea is replaced via an incision in the periphery of the eye. In some embodiments, the incision has an area size which is smaller in more than 70% from the area size of the replaced portion of the cornea. It would talk about size of hole relative to size of area treated and/or angular size (surrounding center of treated area): <180 degrees According to some embodiment, the in-vitro formed implant comprises a bio-compatible scaffold. Optionally, the scaffold comprises one or more types of cells seeded on the scaffold and cultured in-vitro. In some embodiments, the one or more cell types comprise stromal cells, stem cells, mesenchymal stem cells, human embryonic stem cells, induced pluripotent stem cells, cells, placenta-derived cells, for example the PLX-PAD cells (a product of Pluristem Therapeutics Inc.) and/or endothelial cells. Alternatively or additionally, the bio-compatible scaffold comprises or is formed from extracellular matrix (ECM) proteins, for example collagen, recombinant human collagen type I (RHC I) protein, recombinant human collagen type II recombinant human collagen type III, recombinant human collagen type IV or any type ECM protein. Optionally, the scaffold is biodegradable.

According to some example embodiments, the implantation of the HDC lenticle or the scaffold is used for stromal replacements, for example for the correction of the corneal shape and the refractive abnormalities of the eye in subjects with keratoconus I Grade 3, Grade, 4 and/or Grade PLUS according to the RETICS classification.

According to some example embodiments, the implantation of the HDC lenticule or the in-vitro implant is directly into the stroma of the cornea with no access or minimal access of the transplanted tissue to the outer corneal surfaces. Additionally, cells from the corneal surface are optionally introduced into the stroma. In some embodiments, the volume of the implanted tissue is less in at least 10%, at least 20%, at least 50% or any intermediate, smaller or larger percentage value from the corneal volume transplanted in (D)ALK thus having a lower risk for antigen-presenting cells to be a factor in the indirect pathway of rejection.

According to some embodiments, the implantation of the HDC lenticule or the in-vitro implant is performed using a Small Incision Lenticule Extraction (SMILE) procedure. In some embodiments, a small incision having a length in a range of 1 mm-4 mm, is performed in the cornea at a distance of at least 4 mm, for example at least 4.5 mm, at least 5 mm or any intermediate, smaller or larger distance to a center of the recipient cornea. In some embodiments, a center of a cornea is a geometrical position located at equal distances from two locations on the periphery of the cornea that are also positioned on a maximal dimension of the cornea, for example on a diameter of the cornea. In some embodiments, the cornea implant is inserted through the incision into the recipient cornea.

An aspect of some embodiments relates to forming a stromal replacement treatment zone in a cornea, and/or a cornea implant, having a width larger than 7 mm, for example larger than 8 mm, larger than 9 mm or any intermediate, smaller or larger value. In some embodiments, the stroma replacement treatment zone is formed in a cornea of an adult eye. In some embodiments, the stromal replacement treatment zone comprises an implantation bed in a recipient cornea for the cornea implant.

According to some embodiments, a thickness of the formed treatment zone and/or the cornea implant varies in a range of 1 $\mu$m to 500 $\mu$m, for example 1 $\mu$m to 100 $\mu$m, 50 $\mu$m to 150 $\mu$m, 120 $\mu$m to 200 $\mu$m, 180 $\mu$m to 300 $\mu$m, 250 $\mu$m to 350 $\mu$m, 300 $\mu$m to 500 $\mu$m, or any intermediate, smaller or larger range of values.

According to some embodiments, a software program controlling the operation of a femtosecond laser, for example the femtosecond laser VisuMax® 500 kHz by CZM AG is modified, for example to allow the formation of a treatment zone with a width or a maximal dimension, for example a diameter larger than 7 mm, for example larger than 8 mm, larger than 9 mm, larger than 10 mm or any intermediate, smaller or larger value. Additionally, the width or maximal dimension is larger than 7 mm but smaller than a maximal width or a maximal diameter of the cornea. Additionally or alternatively, a software program controlling the operation of an excimer laser, for example MEL® 80 by CZM, is adjusted to allow an ablation profile larger than a width or a maximal dimension of 7 mm.

According to some example embodiments, at least one parameter of a software program controlling the laser is modified, for example a safety zone area or dimensions and/or a programmed ablation area defined by the software. In some embodiments, the at least one parameter is modified, for example automatically modified, when a cornea holder on which a cornea implant is positioned is visualized by the laser.

According to some example embodiments, the formed treatment zone has a round, oval and/or a polygonal shape.

In some embodiments, a cornea implant is shaped to match the dimensions and shape of the formed treatment zone.

According to some embodiments, an incision to insert a cornea implant is performed at the periphery of a recipient cornea at a distance larger than 4 mm, for example larger than 4.5 mm, larger than 5 mm from the center of the cornea. In some embodiments, the incision is performed at a periphery of a visual field of the eye, for example at a distance of less than 8 mm, for example less than 7 mm, less than 5 mm from a border of the visual field.

An aspect of some example embodiments relates to a cornea holder, for example a corneal button jig, shaped and sized for holding at least a portion of cornea. In some embodiments, the cornea holder is shaped and sized to hold at least a portion of a cornea, in a selected fixed curvature along the entire surface of the cornea. In some embodiments, the selected fixed curvature has a radius of curvature in a range of 6 mm-9 mm, for example 6 mm to 8 mm, 7 mm to 8.5 mm, 8 mm to 9 mm or any intermediate, smaller or larger range of values. In some embodiments, the radius of curvature is selected based on the curvature of the recipient cornea, or the curvature of the implantation site formed with the recipient cornea.

According to some example embodiments, the cornea holder comprises an alignment portion on an upper surface of the holder, or adjacent to the upper surface of the holder, for example to allow alignment between the upper surface of the holder comprising at least a portion of the cornea, and a coordinate system of a laser device, for example alignment markings of the laser device. Optionally the alignment marking of the laser device are viewable through an eyepiece of the laser device. In some embodiments, the alignment marking is a visual marking. Optionally, the visual alignment marking is used by the laser system. In some embodiments, the alignment marking is a marking that is visible for the eye tracking system of the laser system. Optionally, the marking is emulating a human pupil for the eye tracking system.

According to some example embodiments, the cornea holder comprises one or more rotation alignment markings on the upper surface of the cornea holder or adjacent to the upper surface of the holder, for example to mark a rotation orientation of the cornea during cutting or ablation when positioned on the curved surface of the holder.

According to some example embodiments, the cornea holder comprises means to avoid that excimer laser radiation which is irradiated onto the periphery of the blank is causing ablation of holder material. For example, some water covers the holder material in the annular surrounding of the blank to protect the holder material from being ablated during the machining of the blank. Alternatively, the annular surrounding of the blank is designed to reflect the excimer laser radiation effectively. The radial width of this annular zone is at least the half diameter of the excimer laser spots, for example at least the diameter of the laser spot.

An aspect of some embodiments relates to ablating a cornea implant positioned in a fixed curvature during the ablating. In some embodiments, the cornea implant is placed on a curved surface during the ablation process. In some embodiments, an ablating sequence of the cornea is applied based on translated coordinates of the fixed curvature.

A potential problem sometimes found with immunological rejection and customization of the anterior lamellar keratoplasty procedure is potentially addressed with the introduction of a Sutureless Intrastromal Anterior Lamellar Keratoplasty (sIALK) described herein. This laser refractive surgery procedure is performed with, for example, a combination of laser profiles of the femtosecond laser VisuMax® 500 kHz and the excimer laser MEL® 80 by CZM, for example for customized stromal exchange and replacement, through a very small single incision in the periphery of the cornea. Additionally, the surgical procedure is performed to compensate for the loss of tissue, while preserving the functioning endothelial cells. In some embodiments, ablation and cutting of the cornea implant are performed while the cornea implant is placed in a fixed curvature on the cornea holder. In some embodiments, cutting and ablation of the cornea implant are performed while the cornea implant is placed in an artificial corneal chamber.

A potential advantage of the suggested new customized sIALK with a free-form HDC lenticule or an in-vitro scaffold is that it replaces and compensates the lost corneal stoma and optionally regenerates the cornea to restore and establish the normal function of the eye. The sIALK procedure potentially allow advanced customization of the anterior lamellar keratoplasty procedure. This advanced customization does not only utilize the geometrical variability of SMILE lenticules but go beyond sphere, cylinder and spherical aberration variability.

A potential advantage of using mesenchymal stromal cells or stem cells seeded on a scaffold for intrastromal implantation, is that these cells may allow regeneration of at least some of the layers of the cornea, for example epithelium, stroma or endothelial layers and the extracellular matrix.

According to some embodiments, a cornea implant, for example a cornea implant lenticule is selected to include one or more of cornea layers. In some embodiments, an in vitro scaffold with cells is selected to include tissue having several layers of the cornea or, multiple in-vitro scaffolds are selected for implantation, each containing a different layer.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Example General Process for Reshaping and Implantation:

According to some example embodiments, a stromal replacement surgery is performed on a human cornea, for example to replace at least a portion of the cornea with an HDC or with a bio-compatible scaffold. In some embodiments, each of the HDC or the bio-compatible scaffold are geometrically reshaped prior to implantation in the recipient cornea.

According to some example embodiments, the stromal replacement surgery comprises an Intrastromal Anterior Lamellar Keratoplasty (IALK), for example a sutureless IALK (sIALK). In some embodiments, the sIALK is an experimental refractive laser surgery procedure, through a very small laser assisted incision of at least 1.5 mm, for example at least 2 mm, at least 2.4 mm or any intermediate, smaller or larger value, in the peripheral cornea. In some embodiments, the stromal replacement surgery is used, for example, to correct one or more corneal protrusions and/or the loss of stroma in keratoconus. Additionally or alternatively, the surgery is used, for example, to correct the corneal shape and/or the refractive abnormality of the eye, for example by adding a HDC lenticule or a RHC I scaffold.

Figure 2:
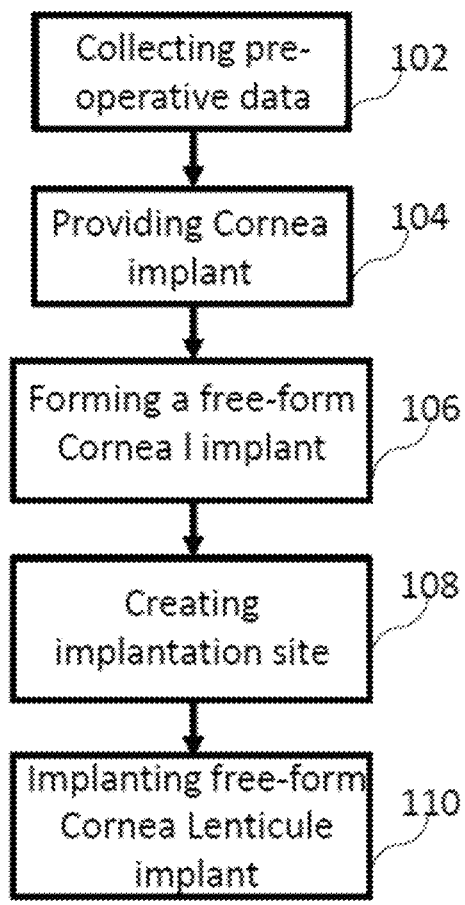
FIG. 2 is a flow chart of a process for reshaping a cornea implant prior to implantation and implantation, according to some example embodiments of the invention.

According to some example embodiments (as shown in FIG. 2), pre-operative data is collected at block 102. In some embodiments, the pre-operative comprises clinical information regarding the clinical condition of an eye and/or clinical condition of the cornea. Additionally or alternatively, the pre-operative data comprises data regarding to one or more damaged regions in the cornea. In some embodiments, the pre-operative data comprises structural information regarding the one or more damaged regions, for example thickness of the cornea, width of the damaged region, diameter of the damaged region, area and/or size of the damaged region, axial length of the eye, crystalline lens anterior and posterior radius of curvature, thickness of the lens and/or diameter of the lens.

According to some example embodiments, the pre-operative data is collected at block 102 using one or more imaging techniques, for example one or more imaging techniques of the eye and/or cornea. In some embodiments, the one or more imaging techniques comprise optical coherence tomography (OCT) and/or low resolution anterior segment Pentacam scheimpflug camera.

According to some example embodiments, a cornea implant, for example a donor cornea or a bio-compatible scaffold is provided at block 104. In some embodiments, the donor cornea comprises a human donor cornea (HDC). Alternatively, the cornea implant comprises an animal cornea, for example a pig cornea. Optionally, the animal cornea is used in a xenotransplantation procedure, and is implanted in a human eye.

According to some example embodiments, the bio-compatible scaffold comprises an in-vitro fabricated scaffold, for example using bioprinting techniques. In some embodiments, the bio-compatible scaffold is formed by decellularization of a tissue, for example tissue of the eye or cornea tissue. In some embodiments, the scaffold comprises one or more extracellular matrix (ECM) proteins, for example collagen. In some embodiments, the scaffold comprises one or more cell types, seeded and cultured in-vitro on the scaffold. In some embodiments, the one or more cell types comprise primary cells, mesenchymal stromal cells, mesenchymal stem cells, induced pluripotent stem cells, embryonic-originated cells, placental-derived cells, immune system-related cells, and/or endothelial cells.

According to some example embodiments, a free-form cornea implant, for example a free-form cornea lenticule implant, is formed at block 106. In some embodiments, the free-form cornea implant is formed in-vitro from the provided cornea implant. In some embodiments, the free-form cornea implant is formed by geometrical reshaping, for example in an X-Y plane of the external surface of the provided cornea implant. In some embodiments, the geometrical reshaping is used to adjust the thickness of the cornea implant, for example along the X-Y plane. Additionally, the dimensions, for example size, width and/or diameter, of the cornea implant are adjusted, for example by cutting the provided cornea implant along a z-axis. In some embodiments, the dimensions of the of the cornea implant are adjusted to fit or according to dimensions of a portion in a recipient cornea, selected to be replaced by the free-form cornea implant.

According to some example embodiments, the geometrical reshaping is performed based on the pre-operative data collected at block 102, for example based on data related to the thickness of the cornea, width of the damaged region, diameter of the damaged region, area and/or size of the damaged region. In some embodiments, the geometrical reshaping is performed using an excimer laser. In some embodiments, the cornea implant is reshaped to have a width or a diameter larger than 7 mm, for example larger than 8 mm, larger than 9 mm or any intermediate, smaller or larger diameter.

According to some example embodiments, an implantation site is created at a recipient cornea at block 108. In some embodiments, the implantation site is created based on the pre-operative data collected at block 102, for example based on a thickness, size and/or shape of a damaged area in the recipient cornea. In some embodiments, the implantation site is generated to have a width or a diameter larger than 7 mm, for example larger than 8 mm, larger 9 mm or any intermediate, smaller or larger diameter. In some embodiments, the thickness of the implantation site generated at block 108 has a diameter or width which is larger than a diameter or width of the cornea implant in up to 100 µm, for example up to 90 µm, up to 80 µm, up to 70 µm, up to 50 µm, up to 40 µm, up to 30 µm or any intermediate, smaller or larger value.

According to some example embodiments, the free-form cornea implant is implanted in a recipient cornea at block 110. In some embodiments, the cornea implant is implanted into the recipient cornea through an incision having a size in a range of 1.5 mm to 5 mm, for example 2 mm to 2.6 mm, 2.4 mm to 3 mm, 2.7 mm to 3.5 mm, 3 m to 4.5 mm, 4 mm to-5 mm or any intermediate, smaller or larger cut in the peripheral cornea. In some embodiments, the incision is formed at a distance of at least 4 mm, for example at least 4.5 mm, at least 5 mm from a center point of the eye.

Figure 3:
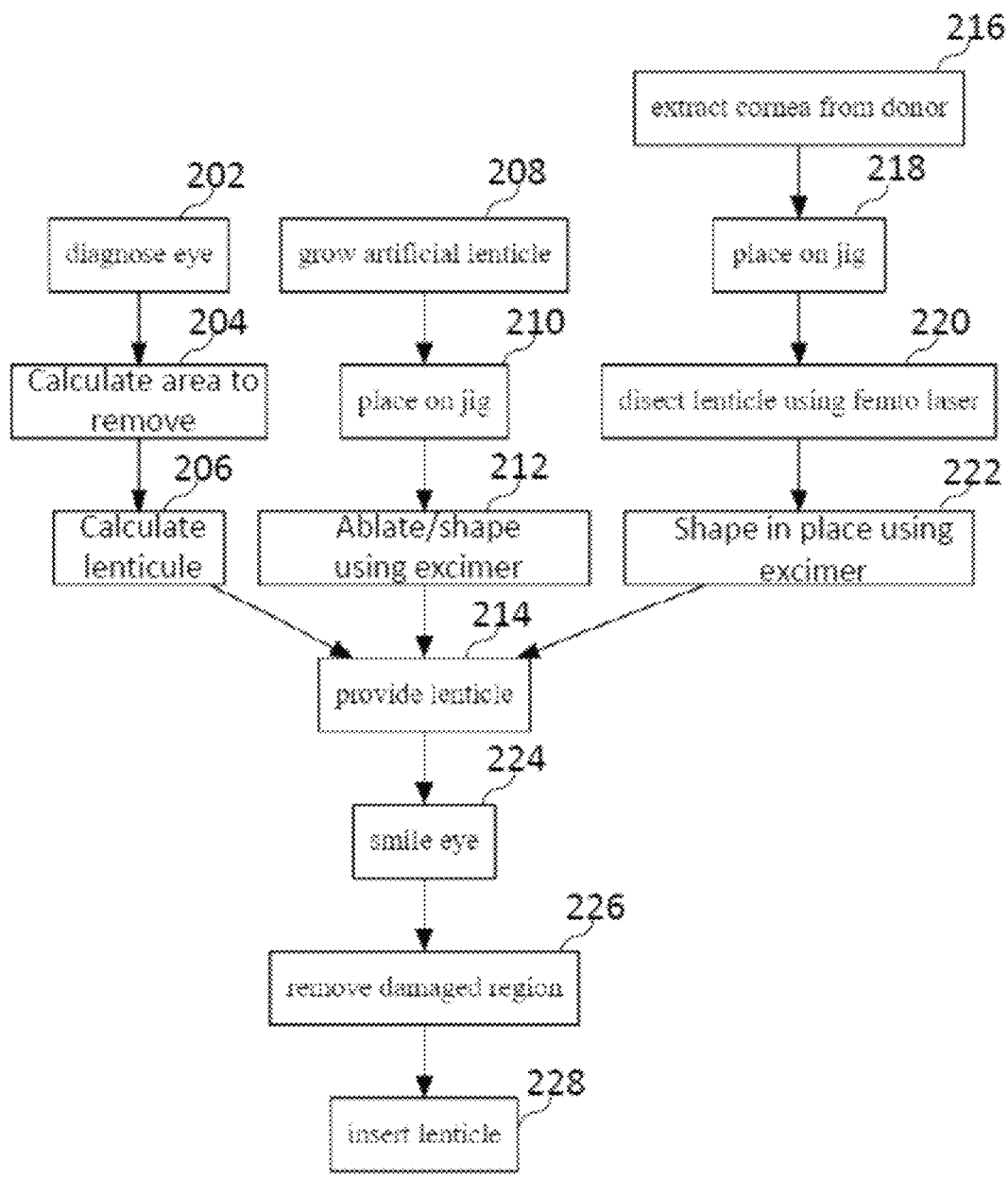
FIG. 3 is a detailed flow chart of a process for reshaping a cornea implant prior to implantation and implantation, according to some example embodiments of the invention.

Example Detailed Process for Reshaping and Implantation of a Cornea Implant:

According to some example embodiments (as shown in FIG. 3), an eye of a subject, for example a cornea of the eye, is diagnosed at 202. In some embodiments, the eye is diagnosed by one or more imaging techniques, for example using OCT. In some embodiments, the OCT comprises high-resolution anterior segment OCT diagnostics. In some embodiments, the eye is diagnosed to detect one or more damaged regions in the cornea. Alternatively or additionally, the eye is diagnosed, for example, in order to determine values of structural parameters of the cornea, for example thickness of the cornea, thickness of one or more damaged regions of the cornea, size, surface and/or shape of the one or more damaged regions and/or size, surface and/or shape of other cornea regions, for example regions surrounding the one or more damaged regions of the cornea. In some embodiments, data collected during diagnosis is used to customize the stromal replacement procedure for a specific cornea of a specific subject.

According to some example embodiments, the eye is diagnosed at block 202 for example to determine corneal shape and/or for detecting refraction abnormalities of the eye. Additionally or alternatively, the eye is diagnosed, for example, to determine a class or a grade of keratoconus. In some embodiments, the eye is diagnosed to determine cell types of the cornea, and/or to determine the shape, thickness, size, width and/or length of various tissue layers of the cornea.

According to some example embodiments, values of one or more parameters related to an area to be removed from the cornea, for example a treatment zone, are calculated at block 204. In some embodiments, the one or more parameters of the treatment zone comprise structural and/or anatomical parameters. In some embodiments, the treatment zone parameters comprise size, shape, curvature angle, surface area, width, diameter and/or depth of the treatment zone. In some embodiments, the calculated values related to the treatment zone are transmitted to a memory of control unit of a laser, for example a femtosecond laser, configured to form the treatment zone in the cornea based on the calculated values.

According to some example embodiments, values of one or more parameters related to a cornea implant, for example a cornea lenticule (in this case the lenticule may also be called "lamella") are calculated at block 206. In some embodiments, the parameters comprise lenticule axis degree, width, diameter, desired thickness along one or more regions on the external surface. In some embodiments, the calculated values of the cornea implant are calculated based on the calculated values of the treatment region parameters. In some embodiments, the calculated values related to parameters of the cornea implant are transmitted to a memory of a control unit of a laser, for example an excimer laser, configured to reshape, for example geometrically reshape the cornea implant based on the calculated values.

According to some example embodiments, an artificial lenticule is grown at block 208. In some embodiments, the artificial lenticule comprises a scaffold, for example a biocompatible scaffold. In some embodiments, the scaffold comprises one or more extracellular matrix (ECM) proteins, for example collagen proteins. In some embodiments, the scaffold comprises a recombinant human collagen type I (RHC I) scaffold. In some embodiments, the scaffold is a biomimetic, biocompatible and surgically transplantable for intrastromal replacement. In some embodiments, the scaffold is fabricated using Laser Induced Forward Transfer (LIFT) 3D printing technology.

According to some example embodiments, the artificial lenticule comprises one or more cell types, for example primary cells, endothelial cells, stromal cells, stem cells, mesenchymal stem cells, stromal stem cells, induced pluripotent stem cells, and/or placenta-derived stem cells. In some embodiments, the cells are seeded on the scaffold and are cultured in-vitro, for example in a bio-reactor, to form a tissue. In some embodiments, the scaffold with the cells is configured to allow regeneration of the three layers of the cornea and optionally also regeneration of the ECM.

According to some example embodiments, the artificial lenticule is placed on a lenticule holder, for example a jig, at block 210.

According to some example, the artificial lenticule is reshaped at block 212. In some embodiments, the artificial lenticule is reshaped using values calculated at block 206. In some embodiments, the artificial lenticule is reshaped, for example by geometrical reshaping of an external surface of the artificial lenticule. In some embodiments, the geometrical reshaping comprises removing of one or more tissue layers. Additionally or alternatively, geometrical reshaping comprises reshaping an outline of the external surface of the artificial lenticule. In some embodiments, the artificial lenticule is geometrically reshaped using an ablating laser. In some embodiments, the artificial lenticule is geometrically reshaped using an excimer laser, for example the excimer laser MEL® 80 by CZM.

According to some example embodiments, an in an alternative approach, a cornea is extracted from a donor at block 216. In some embodiments, a cornea is extracted from a human donor, and is termed HDC. Alternatively, a cornea is extracted from an animal, for example from a pig. Alternatively, a cornea is provided from a cornea bank. In some embodiments, the cornea is provided as a whole cornea. Alternatively, at least 70%, for example at least 75%, at least 85%, at least 90%, at least 95% or any intermediate, smaller or larger percentage of cornea tissue is provided.

According to some example embodiments, the cornea is placed on a cornea holder, for example a cornea jig, at block 218. In some embodiments, the cornea is placed on an upper surface of the cornea holder having a radius of curvature of at least 7 mm, for example at least 8 mm, at least 9 mm, at least 10 mm or any intermediate, smaller or larger radius of curvature.

According to some example embodiments, the cornea is dissected at block 220. In some embodiments, the cornea is dissected while positioned in the cornea holder, for example to form a free-form lenticule at block 220. In some embodiments, the cornea is dissected using a laser, for example a femtosecond laser and/or an excimer laser. In some embodiments, the femtosecond laser comprises the femtosecond laser VisuMax® 500 kHz. In some embodiments, the excimer laser comprises the excimer laser MEL® 80 by CZM.

According to some example embodiments, the cornea is dissected along a z-axis, for example to define a width or a diameter of the cornea implant, for example a lenticule implant. In some embodiments, the cornea implant is dissected into a depth of at least 30 μm, for example at least 50 μm, at least 70 μm, at least 100 μm, at least 120 μm, at least 150 μm, or any intermediate, smaller or larger value. In some embodiments, the cornea is dissected to form a lenticule implant having a diameter or width of at least 6 mm, for example at least 7 mm, at least 8 mm, at least 9 mm or any intermediate smaller or larger value. In some embodiments, the cornea is dissected based on values calculated at block 206.

According to some example embodiments, the lenticule is reshaped, for example geometrically reshaped at block 222. In some embodiments, the lenticule is reshaped while positioned in the cornea holder. In some embodiments, the lenticule is reshaped during dissection, or following a dissection process. In some embodiments, the lenticule is reshaped by removing tissue or ablating tissue along the external surface of the lenticule. In some embodiments, the lenticule is reshaped by removing tissue or ablating tissue along an X-Y plane of the external surface of the lenticule.

According to some—example embodiments, the lenticule is reshaped using a laser, for example an excimer laser. In some embodiments, the laser is configured to ablate a region having an area larger than 7 mm, for example larger than 8 mm, larger than 9 mm or any intermediate, smaller or larger area size. In some embodiments, the excimer laser comprises the excimer laser MEL® 80 by CZM.

According to some example embodiments, a cornea implant is provided at block 214. In some embodiments, the cornea implant comprises a scaffold with or without cells, formed at block 212. Alternatively, the cornea implant comprises a lenticule implant formed at blocks 220 and 222.

According to some example embodiments, a recipient cornea is dissected in a Small Incision Lenticule Extraction (SMILE) surgical process, at block 224. In some embodiments, in the SMILE procedure a laser, for example a femtosecond laser is used to create a small, lens-shaped bit of tissue (lenticule) within the recipient cornea. Additionally, the laser is used to form a small incision, for example an arc-shaped incision in the surface of the cornea through which the created lenticule is extracted. In some embodiments, the incision has a length in a range of 1.5 mm to 5 mm, for example 2 mm to 3.5 mm, 2.4 mm to 4 mm, 3.2 mm to 5 mm or any intermediate, smaller or larger incision length. In some embodiments, the femtosecond laser comprises the femtosecond laser VisuMax® by CZM AG. In some embodiments, the shape and size of the removed lenticule are determined based on the values calculated at block 204.

According to some example embodiments, a damaged region of the recipient cornea is removed at block 226. In some embodiments, the damaged region is part of the lenticule, removed at block 224. In some embodiments, the damaged region is ablated using the femtosecond laser.

According to some example embodiments, the lenticule removed at block 224 and/or the damaged region removed a block 226 define a treatment region in the recipient cornea. In some embodiments, a shape, size, area, width and/or diameter of the treatment region are determined based on the values calculated at block 204, the properties of the cornea implant and/or the diagnosis results of the eye. In some embodiments, the laser, for example the femtosecond laser is configured to form a treatment region that has a width or a diameter larger in up to 150 μm, for example up to 100 μm, up to 50 μm or any intermediate, smaller or larger value from the width or diameter of the cornea implant, for example to allow better implantation of the cornea implant within the treatment region.

According to some example embodiments, the cornea implant is implanted within the target region in the recipient cornea at block 228. In some embodiments, the cornea implant is implanted in a ReLEx SMILE laser refractive surgery procedure. In some embodiments, during implantation the cornea implant is aligned with respect to the recipient cornea by aligning the peripheral incision with a rotation marking in the implant, for example a rotation marking formed at a 0 degrees mark of the cornea holder. Additionally, the cornea implant is dissected to have a width or diameter smaller in at least 50 μm, for example at least 70 μm, at least 100 μm, at least 120 μm or any intermediate, smaller or larger value, from a diameter or width of the implantation bed.

Example Reshaping a Cornea Implant:

According to some example embodiments, a sutureless Intrastromal Anterior Lamellar Kertoplasty (sIALK) procedure, as described in this application, is a laser refractive procedure to correct the loss of the corneal stroma and/or the refractive abnormalities of the eye the in keratoconus. In some embodiments, the procedure is based on imaging results, for example imaging results using high resolution Anterior Optical Coherence Tomography. Reference is now made to FIGS. 4a-4d depicting the formation of a free-form HDC lenticule, according to some embodiments of the invention.

According to some example embodiments, the HDC lenticule, for example an HDC button lamella is formed to have a constant spatial thickness. In some embodiments, a lamellar keratoplasty option of a femtosecond laser system, for example the femtosecond laser system VISUMAX 500 kHz by Carl Zeiss Meditec AG is used.

Figure 4A:
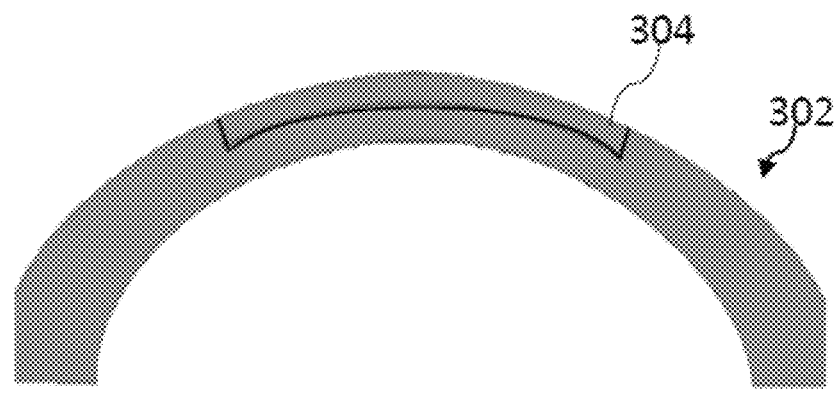
FIGS. 4a-4d are schematic illustrations describing reshaping a cornea implant, according to some example embodiments of the invention.

According to some example embodiments, for example as shown in FIG. 4a, an HDC button lamella, for example HDC button lamella 304, is dissected out from a donor cornea 302. In some embodiments, the dissected HDC button lamella 304 is placed on a cornea holder having a constant radius of curvature of at least 7 mm, for example at least 8 mm, at least 9 mm or any intermediate or smaller value. In some embodiments, the maximal radius of curvature of the cornea holder is up to 15 mm, for example up to 12 mm, up to 10 mm or any intermediate, smaller or larger value.

Figure 4B:
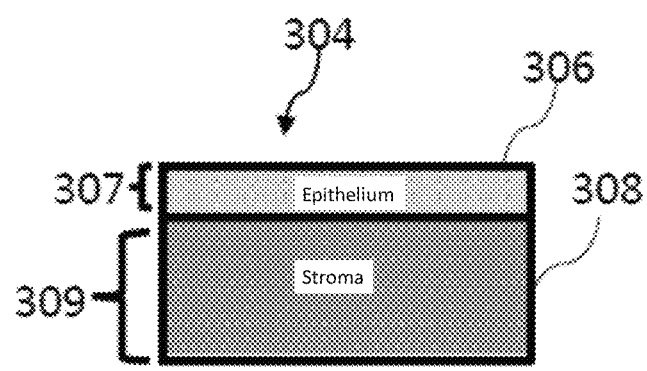

According to some example embodiments, for example as shown in FIG. 4b, the dissected HDC button lamella 304 comprises an upper epithelium layer 306 and a lower stroma layer 308. In some embodiments, a thickness 307 of the upper epithelium layer is in a range of 30 μm to 100 μm, for example 30 μm to 50 μm, 40 μm to 70 μm, 60 μm to 100 μm or any intermediate, smaller or larger range of values. In some embodiments, a thickness 309 of the stroma layer is in a range of 100 μm to 500 μm, for example 100 μm to 200 μm, 150 μm to 300 μm, 250 μm to 450 μm, 350 μm to 500 μm or any intermediate, smaller or larger range of values.

According to some example embodiments, when placed in the cornea holder, the HDC button lamella is marked at 0° degree. In some embodiments, the HDC button lamella is marked at a selected location to set a specific rotational orientation of the HDC button lamella. In some embodiments, the marking is performed, for example, in order to be sure that there will be no induced rotation error mistake of the free-form lenticule at the time of the implantation.

According to some example embodiments, the epithelium layer of the HDC button lamella is removed, for example by ablation. In some embodiments, the epithelium layer of the HDC button lamella is ablated with a constant spatial thickness in a range of 50 μm to 90 μm, for example 50 μm to 70 μm, 60 μm to 80 μm, 65 μm to 75 μm, 74 μm to 85 μm or any intermediate, smaller or larger range of values. In some embodiments, the epithelium layer is ablated with a constant thickness of 70 μm. Alternatively, the epithelium layer is ablated with a varying thickness along the surface of the HDC button lamella. In some embodiments, the ablation thickness is calculated, for example at blocks 206 and/or 204 shown in FIG. 3. In some embodiments, the epithelium layer is ablated using the excimer laser MEL-80 by Carl Zeiss Meditec AG.

Figure 4C:
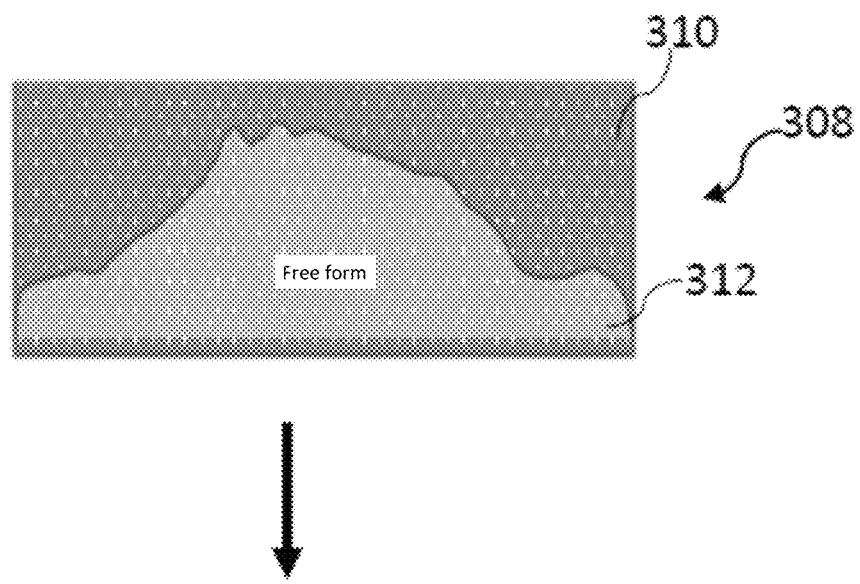
Figure 4D:
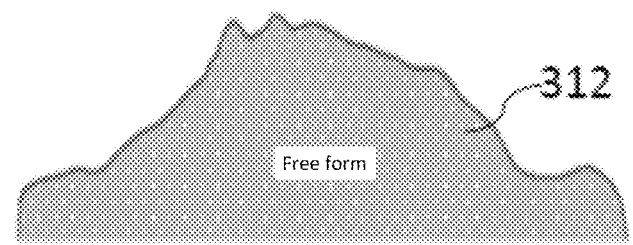

According to some example embodiments, for example as shown in FIGS. 4c and 4d, the HDC button lamella is ablated to achieve a cornea implant, for example a free-form HDC lenticule. In some embodiments, the HDC button lamella 308 is reshaped by ablating tissue 310 on the upper portion of the HDC button lamella, for example to form the free-form HDC lenticule 312 (the lamella to be implanted). In some embodiments, an outline of the free-form HDC lenticule is reshaped according to the values calculated at block 206 shown in FIG. 3. In some embodiments, the free-form HDC lenticule is reshaped using an excimer laser, for example the excimer laser MEL-80 by Carl Zeiss Meditec AG.

Figure 5A:
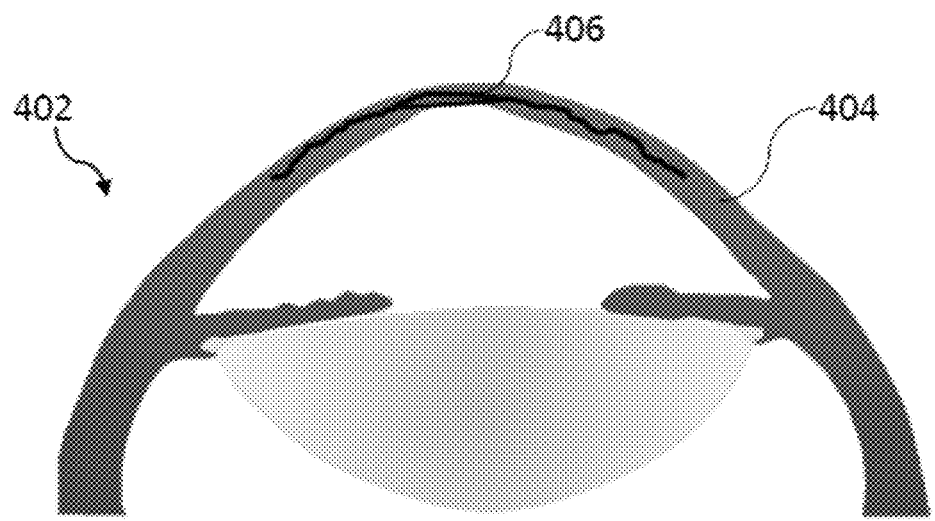
FIG. 5a is a schematic illustration showing dissection of a cornea of a recipient, according to some example embodiments of the invention.

Example Implantation Bed Creation and Implantation of HDC Lenticule (Lamella):

Reference is now made to FIG. 5a depicting creation of the implantation bed, according to some example embodiments.

According to some example embodiments, a recipient cornea is dissected to create an implantation site, for example an implantation bed for the cornea implant, for example the free-form HDC lenticule. In some embodiments, the recipient cornea is dissected according to values calculated for example at block 204 shown in FIG. 3. In some embodiments, a width or a diameter of the implantation site is larger than a width or diameter of the cornea implant in up to 200 μm, for example up to 150 μm, up to 100 μm, up to 80 μm or any intermediate, smaller or larger value.

According to some example embodiments, the implantation site 406 is formed using a femtosecond laser, for example the femtosecond laser system VISUMAX 500 kHz by Carl Zeiss Meditec AG. Optionally, the procedure for generating the implantation site is the ReLEx Smile procedure. In some embodiments, during the procedure a −0.75D sphere manifest refraction correction is performed.

According to some example embodiments, during the procedure a tissue lenticule having a diameter in a range of 7 mm to 9 mm, for example 7 mm to 8 mm, 7.5 mm to 8.5 mm or any intermediate, smaller or larger range of values is generated by dissecting the cornea 404 of eye 402. In some embodiments, a cap diameter is in a range of 8 mm to 10 mm, for example 8 mm to 9 mm, 8.5 mm to 9.5 mm, 8.5 mm to 9 mm or any intermediate, smaller or larger range of values. (8.7 mm). In some embodiments, a tissue having a thickness in a range of 30 µm to 50 µm, for example 40 µm, 42 µm or any intermediate, smaller or larger value is extracted from the center portion of the implantation site. Additionally, a tissue having a thickness in a range of 15 µm to 30 µm, for example 20 µm, 25 µm or any intermediate, smaller or larger value is extracted from the edges of the implantation site.

Figure 5B:
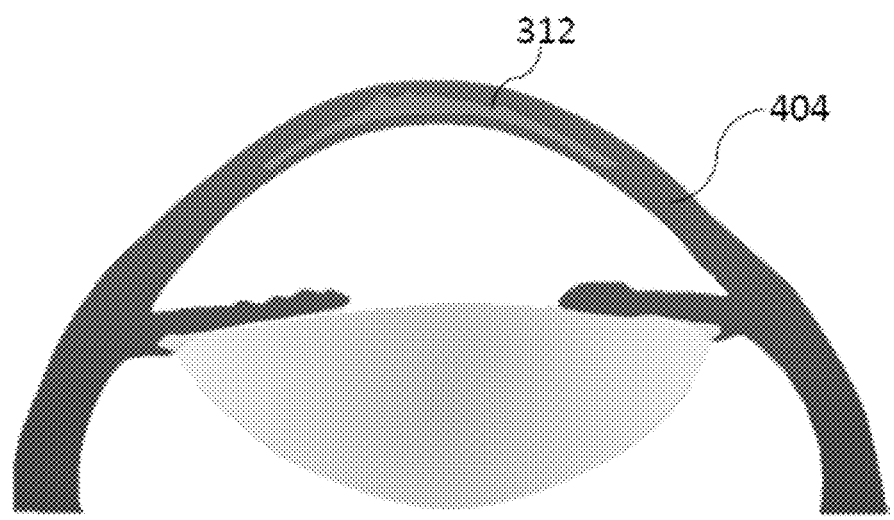
FIG. 5b is a schematic illustration showing implantation of a reshaped implant into a dissected cornea, according to some example embodiments of the invention.

According to some example embodiments, an incision in the recipient cornea, for example in the periphery of the recipient cornea is performed. In some embodiments, the incision length is in a range of 2 mm to 4 mm, for example 2 mm to 3 mm, 2.3 mm to 3.2 mm, 3 mm to 4 mm or any intermediate, smaller or larger range of values. In some embodiments, the incision is performed, for example to allow the removal of the lenticule from the recipient cornea and the implantation of the cornea implant. In some embodiments, the incision is performed at a location selected to be aligned with the rotation orientation marking performed in the cornea implant, for example the marking performed at 0° degree. According to some example embodiments, for example as shown in FIG. 5b, the free-form cornea implant, for example the free-form HDC lenticule 312 shown in FIGS. 4c and 4d is implanted into the recipient cornea 404. In some embodiments, the implantation of the free-form lenticule is performed by tweezers. In some embodiments, during the implantation the free-form lenticule is oriented in the center of the side cut. In some embodiments, in order to achieve a correct match between the HDC lenticule and the implantation bed, the width or diameter of the implantation bed is at least 0.05 mm, for example at least 0.1 mm larger than the implanted lenticule diameter width or diameter.

Figure 6A:
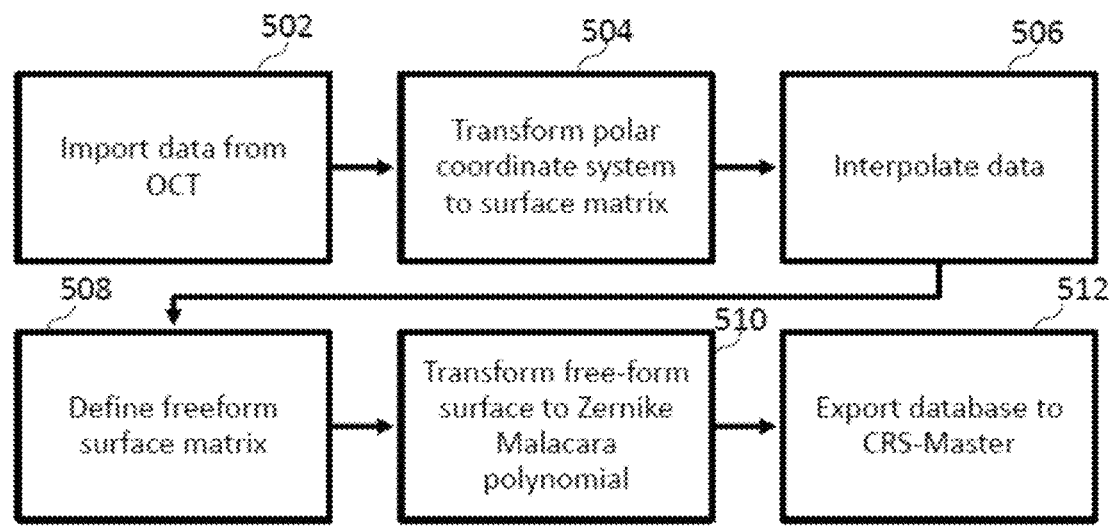
FIG. 6a is a flow chart of a process for defining structural parameter values of a desired implant, according to some example embodiments of the invention.

Example Defining a Desired Shape of a Corneal Implant:

According to some example embodiments, pre-operative data is collected, for example using one or more imaging techniques, for example as described at block 202 shown in FIG. 3, and block 102 shown in FIG. 2. In some embodiments, the imaging technique comprises high resolution anterior segment optical coherence tomography using, for example, the OCT Casia 2 (Tomey GmbH) system. In some embodiments, Matlab (MathWorks, Inc.) is used to write one or more scripts for performing calculations based on the OCT data. Reference is now made to FIG. 6a, depicting a process for manipulating OCT data, according to some embodiments of the invention.

According to some example embodiments, configuration of OCT is performed, for example in order to have better resolution on radial scans (B/C scans=256). Additionally or alternatively, configuration of OCT is performed, for example to reach fast speed of measurement (A/B scans=512). In some embodiments, fast speed of measurements is needed, for example to minimising errors due to the movement of patient eye.

According to some example embodiments, data is imported from the OCT to an analysis and/or calculation software, for example a MATLAB software, at block 502.

According to some example embodiments, OCT provides raw data maps in a polar coordinate system, for example maps with information about corneal SAG and/or thickness of the cornea. In some embodiments, a MATLAB Script takes this data and creates a grid matrix, for example a 256 by 256 grid matrix, at block 504. In some embodiments, following grid formation, the data undergoes an interpolation process at block 506.

According to some example embodiments, in order to calculate a distribution of the normal corneal thickness we use information from the article by Ambrosio R Jr. et al. (J Cataract Refract Surg. 2006) with optionally statistically rich data. In some embodiments, a benchmark matrix (CTSP) is created with the same size as OCT data, for example in a size of 256 by 256, for example at block 508. In some embodiments, the script subtracts the patient corneal thickness matrix with the benchmark one (CTSP) and creates a new matrix with missing tissue (WTPM). Additionally, the matrix includes a hydration coefficient and the spatial thickness profile of the removed ReLEx Smile lenticule.

According to some example embodiments, the free-form surface is transformed to Zernike Malacara polynomial at block 510.

According to some example embodiments, the database is exported to a treatment planning software, for example a CRS-Master, at block 512.

Excimer Laser Management:

According to some example embodiments, the excimer laser operation is controlled by a treatment management software, for example by the CRS-Master software. In some embodiments, the CRS-Master is a treatment planning software for the MEL-80 (Carl Zeiss Meditec AG) excimer laser. In some embodiments, the CRS-Master is configured to plan conventional and customized laser vision corrections, for example LASIK, Femto-LASIK, PRK and LASEK. The software has several options for laser vision correction with feedback from the ocular aberrometer WASCA (Carl Zeiss Meditec AG) and the corneal topography ATLAS 9000 (Carl Zeiss Meditec AG).

According to some example embodiments, the software is used for customized wavefront driven laser vision correction. In some embodiments, the Software represents ocular wavefront error using the Zernike Malacara polynomial notation to 6th order. In some embodiments, in most of the wavefront refractive surgery techniques is applied the phase conjugation principle. In some embodiments, compensation of all points of optical path difference of the total ocular aberration are done by topographic change of cornea.

According to some example embodiments, a treatment profile of ablation for wavefront vision correction applied to the stroma tissue are scaled by a factor of 2.9631 from ocular aberration.

$$1/n_{cornea}^{-1} = 1/1.3375 - 1 = 2.9631$$

In some embodiments, from that point, to implement free-form ablation profile surface as wavefront error It will need (WTPM) to be divided by factor 2.9631. Additionally, in the next step, transformation of matrix (WTPM) to Zernike Malacara notation is performed, for example to match data submission for CRS-Master.

According to some e example embodiments, after that manipulation, a script creates a database via add-on Database explorer for Matlab. In some embodiments, the CRS-Master recognize database as ocular abberometer data and allows to create free-form lenticule with the excimer laser.

Figure 6B:
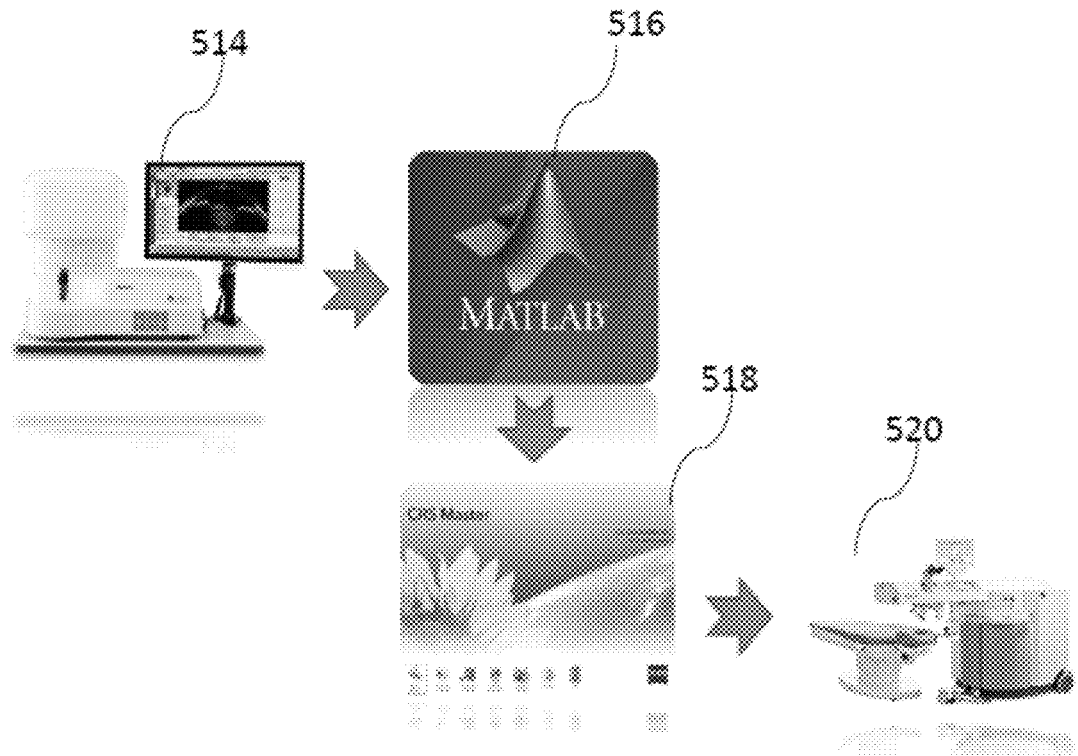
FIG. 6b is a flow chart of a process for transforming data collected by OCT to an ablation profile to be used by a laser device, according to some example embodiments of the invention.

According to some example embodiments, for example as shown in FIG. 6b, data from OCT 514 is imported to an analysis software, for example MATLAB analysis software 516. In some embodiments, a database generated by the software is delivered to a treatment management software, for example the CRS-master software 518. In some embodiments, information regarding a treatment profile of ablation generated by the CRS master software is transmitted to a memory of a control unit of an excimer laser 520. In some embodiments, control unit of the laser is configured to activate the laser according to the treatment profile of ablation.

Figure 6C:
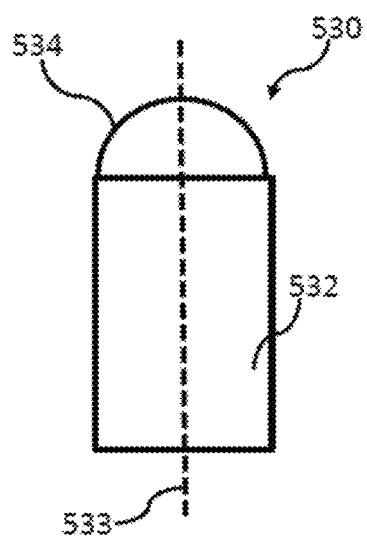
FIGS. 6c-6e are schematic illustrations of a cornea lenticule holder, according to some example embodiments of the invention.
Figure 6D:
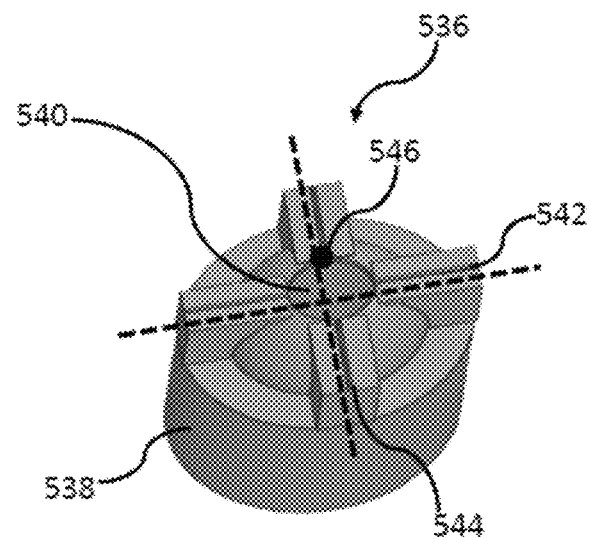
Figure 6E:
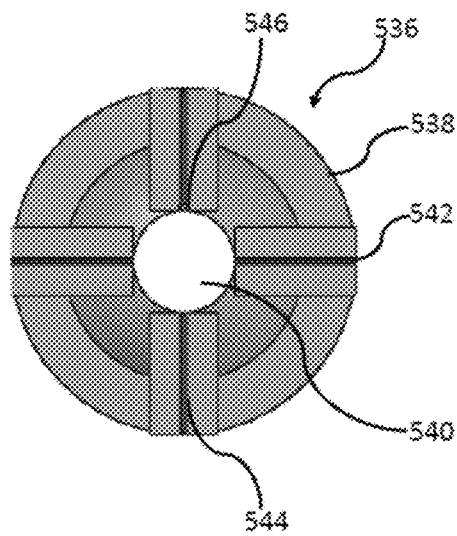

Example Cornea Lenticule Holder:

According to some example embodiments, the lenticule holder is shaped and sized for dissecting and/or reshaping a cornea while the cornea is positioned on a curved surface of the lenticule holder. In some embodiments, the curved surface is curved along at least 50% of the surface area. In some embodiments, placing the cornea on a curved surface during dissecting and/or reshaping allows for example, to have accurate dissecting and/or reshaping by one or more of preventing movement of the lenticule in a z-axis during the procedure, maintaining a known thickness of the cornea along the entire cornea surface during the procedure, and keeping the cornea in a desired curvature that allows better functionally post implantation. Reference is now made to FIGS. 6c-6e, depicting parts of a cornea holder, according to some embodiments of the invention.

According to some example embodiments, a cornea holder, for example a cornea lenticule holder comprises a cornea holder base 530, shaped and sized for holding a cornea in a fixed curvature during dissection and/or ablation. In some embodiments, the cornea holder base 530 comprises a body 532 having a longitudinal axis 533 and an upper curved surface 534. In some embodiments, the upper curved surface has a radius of curvature in a range of 7 mm to 9 mm, for example 7 mm to 8 mm, 7.5 mm to 8.5 mm, 7.8 mm to 8.3 mm, 7.9 mm to 9 mm or any intermediate, smaller or larger range of values. In some embodiments, the upper curved surface 534 is configured to hold a cornea or a portion of cornea, for example a cornea lenticule.

According to some example embodiments, for example as shown in FIGS. 6d and 6e, the cornea holder comprises an alignment portion located near or adjacent to the curved surface 534. In some embodiments, the alignment portion is part of a cornea holder alignment cover 536, configured to be placed on top the cornea holder base 530. In some embodiments, the holder alignment cover is hollow, for example to allow placing the cover around the holder base. In some embodiments, the cornea holder alignment cover 536 comprises a base 538 having a longitudinal axis, and a central opening 540 at the upper surface of the cover 536. In some embodiments, the central opening 540 comprises a round or an oval opening. In some embodiments, the central opening 540 is shaped and sized to allow at least a partial penetration of a cornea positioned on the curved surface of the holder base from within a lumen of the cover 536. Alternatively or additionally, the central opening 540 is shaped and sized to allow at least a partial penetration of the curved surface 534 through the opening from within a lumen of the cover 536. Optionally, the central opening 540 and the upper curved surface 534 are co-axial, when the cornea holder base is positioned at least partially within the lumen of the holder alignment cover 536.

According to some example embodiments, the alignment portion comprises at least one, for example at least two alignment markings located on the upper curved surface 534 or adjacent to the upper curved surface 534. In some embodiments, the alignment markings are shaped as elongated indentations or channels. Optionally, the alignment markings comprise at least two straight lines or channels, shaped and sized to allow alignment of the upper curved surface with alignment marking or a coordinate system of a laser surgical device. Additionally or alternatively, the alignment portion comprises one or more rotation orientation markings located on the upper curved surface 534 or adjacent to the upper curved surface 534. In some embodiments, the rotation orientation marking is shaped as an opening or an indentation, and configured to mark a selected orientation position of the cornea or the cornea implant placed on the upper curved surface. In some embodiments, the orientation position of the cornea implant is marked to maintain a fixed rotation orientation of the cornea implant with respect to the cornea holder during the cutting and/or reshaping procedure. Additionally, the rotation orientation marking allows rotational alignment between the cornea implant and a marking in the eye, for example a peripheral incision formed in the eye to allow, for example implantation of the cornea implant into a recipient cornea.

According to some example embodiments, the cover 536 comprises at least two alignment channels on the upper surface, crossing through the central opening 540 and positioned at a known angle relative to each other. Optionally, the at least two channels, for example channels 542 and 544 are perpendicular to each other. In some embodiments, the two alignment channels form a cross. In some embodiments, the center of the cross is positioned at a center of the central opening 540. In some embodiments, the alignment channels are shaped and sized to allow alignment with a cross-shaped marking in an eye-piece of a laser device, for example to allow better focusing and/or accurate dissection or ablation.

According to some example embodiments, the upper surface of the cover 536 comprises one or more marking indentations or marking openings on an edge of the central opening 540, for example marking opening 546. In some embodiments, the marking is positioned at an intersection between an alignment channel, for example an alignment channel 542 and the central opening 540.

Figure 6F:
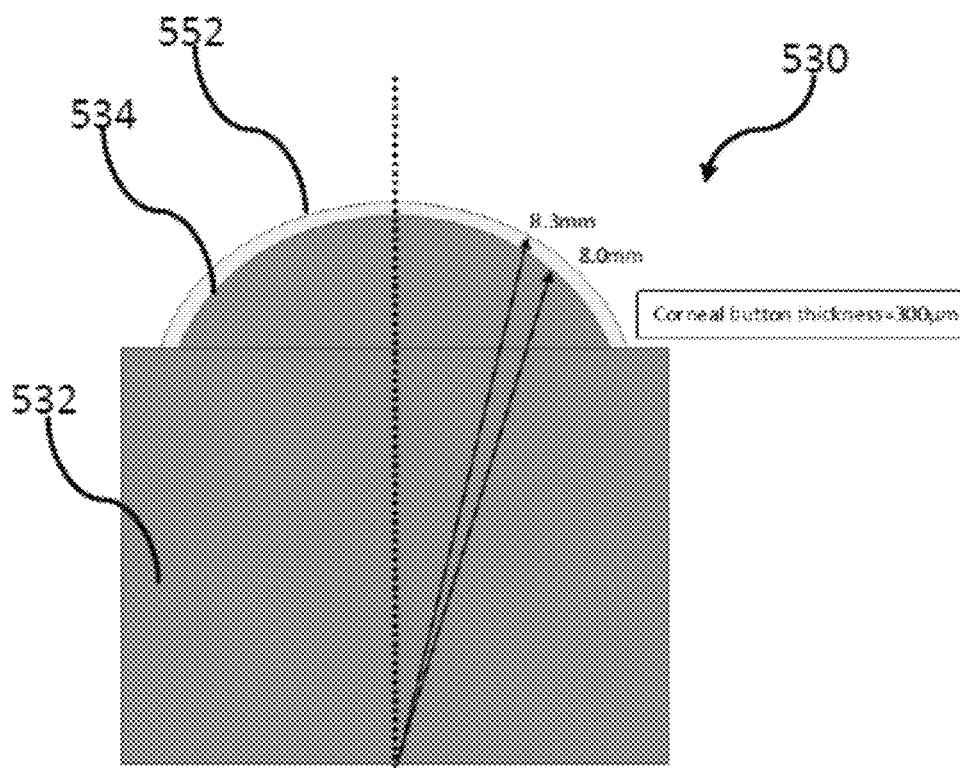
FIG. 6f is a schematic illustration of a cornea positioned on an upper curved surface of a cornea holder, according to some example embodiments of the invention.

According to some example embodiments, the cover 536 and the base 530 are fixed relative to each other when the base 530 is positioned within the cover 536, for example to prevent relative movement between them during laser activation According to some example embodiments, for example as shown in FIG. 6f, a cornea 552 is placed on top a curved surface 534 of a cornea holder base 530. In some embodiments, the curved surface 534 allows to maintain a constant thickness of the cornea throughout the entire surface area of the cornea.

It is expected that during the life of a patent maturing from this application many relevant methods for dissecting and ablating a cornea will be developed; the scope of the terms dissecting and ablating is intended to include all such new technologies a priori.

As used herein with reference to quantity or value, the term "about" means "within +/− 10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range. Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

Features related to and characterized for the system apply in analogy to the relevant method, while method features may be applied as functional features of the system described accordingly.

What is claimed is:

1. A planning unit for generating control data for a system for laser surgery of an eye, including for keratoplasty, comprising:
    a first laser device and at least one characterization device;
    wherein the first laser device is configured to generate at least one incision in a cornea and is controllable by the control data; and
    wherein the planning unit comprises:
        a first interface that supplies first measurement data on corneal parameters from the at least one characterization device;
        a second interface that supplies second measurement data or model data of a lamella, insertable into a cornea after generation of the incision;
        a third interface that transfers control data to the first laser device; and
        a computing circuitry that determines the at least one incision in the cornea using the first measurement data and second measurement data or model data, wherein the computing circuitry generates a control data set configured to control the first laser device;
    wherein the control data set facilitates generation of the at least one incision by the first laser device using the control data set;
    wherein a first device coordinate system of the first laser device and a second device coordinate system of the at least one characterization device are coupled using registration and the supplied second measurement data or model data of the lamella can be unambiguously registered to the first device coordinate system and the second device coordinate system;
    wherein the system for laser surgery further comprises a second laser device;
    wherein the planning unit is further configured to generate control data for the second laser device of the system for laser surgery of an eye, wherein the second laser device processes a blank to create a patient-specific formed lamella that is to be implanted into the cornea; and
        wherein the planning unit comprises a fourth interface for transferring control data to the second laser device;
        wherein a third device coordinate system of the second laser device is also coupled using registration to the first device coordinate system of the first laser device and the second device coordinate system the characterization device.

2. The planning unit according to claim 1, wherein the first laser device comprises a femtosecond laser.

3. The planning unit according to claim 1, wherein the at least one characterization device comprises an optical coherence tomography (OCT) device.

4. The planning unit according to claim 1, wherein the second laser device comprises an excimer laser.

5. The planning unit according to claim 1, wherein the incision to be generated in the cornea describes a pocket incision or comprises an anterior and a posterior surface such that the incision forms a corneal volume to be extracted.

6. The planning unit according to claim 1, which is further configured to generate control data for the second laser device such that a defined edge geometry is achieved in the patient-specifically formed lamella, wherein
in the case of a pocket incision, and thus without creating a vacancy, edge thickness is a maximum of 30 µm, or
in the case of an extracted corneal volume, and thus with creation of a vacancy, edge thickness of the lamella is adapted to the vacancy.

7. The planning unit according to claim 6, wherein in the case of the pocket incision, and thus without creating the vacancy, the edge thickness is between 5 µm and 15 µm.

8. The planning unit according to claim 6, which is further configured to determine an annular transition zone at an edge of the lamella within which the edge thickness gradually changes into a patient-specific thickness profile, and further configured to generate control data such that the control data prevents processing of the edge of the lamella by the second laser device.

9. The planning unit according to claim 1, which is further configured to generate control data for a temperature regime to maintain a temperature below a selected maximum temperature while processing the lamella with the second laser device.

10. The method for planning as claimed in claim 9, which is further configured to generate control data for the temperature regime to maintain the temperature in a range from below 40° C. to below 10° C. or to a freezing point of the lamella.

11. The method for planning as claimed in claim 10, which is further configured to generate control data to adjust shot distribution and laser frequency of a scanning spot laser to maintain the temperature regime.

12. The planning unit according to claim 1, which is further configured to generate control data for the second laser device such that an ametropia correction is achieved.

13. The planning unit according to claim 12, which is further configured to generate control data for the second laser device such that a refractive power, an astigmatism or both is applied to the blank.

14. The planning unit according to claim 1, which is further configured to generate control data for a subsequent correction by replacing the inserted lamella with a corrected lamella taking into account stored control data of the inserted lamella.

15. The planning unit according to claim 1, which is further configured to generate control data taking into account a defined initial hydration condition of the blank or the lamella ex-vivo and a change in the hydration condition of the lamella during or after implantation.

16. The planning unit according to claim 15, which is further configured to generate control data taking into account the defined initial hydration condition of the blank or the lamella ex-vivo and the change in the hydration condition of the lamella during or after implantation by using a constant expansion factor.

17. A system for laser surgery of an eye, including for keratoplasty, comprising the first laser device, the second laser device, and the at least one characterization device and the planning unit according to claim 1.

18. The system for laser surgery according to claim 17 further comprising:
a control unit including a memory comprising a treatment program;
wherein said treatment program comprises a program for refractive correction and for dissecting the cornea, ablating the cornea or both to have a treatment zone having a maximal dimension in a range between 8 mm and a maximal dimension of the cornea;
a control circuitry configured to signal a laser device to dissect a cornea, to ablate a cornea or both according to the treatment program, with the treatment program.

19. The system for laser surgery according to claim 17, wherein the control circuitry uses control data generated by the planning unit.

20. A method for planning realizing the generation of control data for a system for laser surgery of an eye, comprising the first laser device, the second laser device and the at least one characterization device, and the planning unit, according to encoding of the planning unit according to claim 1.

21. The method for planning as claimed in claim 20 further comprising generating the control data for keratoplasty.

* * * * *

UNITED STATES PATENT AND TRADEMARK OFFICE
CERTIFICATE OF CORRECTION

| | |
|---|---|
| PATENT NO. | : 12,011,394 B2 |
| APPLICATION NO. | : 17/602874 |
| DATED | : June 18, 2024 |
| INVENTOR(S) | : Angelov et al. |

It is certified that error appears in the above-identified patent and that said Letters Patent is hereby corrected as shown below:

In the Specification

Column 4, Lines 11-17, delete "The currently practiced........within certain limits." and insert the same line at Line 12, as a new paragraph Column 6, Line 27, delete "the art" and insert --art--

Columns 12 & 13, Lines 66-67 & 1-2, delete "an elongated base........a curved orientation." and insert the same at Line 67, as a new sub-point Column 13, Lines 24-25, delete "planning realizing" and insert --planning and realizing--

Column 13, Line 37, delete "eye:" and insert --eye.--

Column 19, Line 47, delete "degrees" and insert --degrees.--

Column 21, Line 47, delete "is causing" and insert --causing--

Column 23, Line 56, delete "of the of the" and insert --of the--

Column 25, Line 58, delete "an in" and insert --in--

Column 29, Lines 29-40, delete "According to some........width or diameter." and insert the same at Line 30, as a new paragraph Column 29, Line 49, delete "Matlab" and insert --MATLAB--

Column 30, Line 61, delete "Matlab." and insert --MATLAB.--

Column 32, Lines 42-43, delete "activation" and insert --activation.--

Signed and Sealed this
Eleventh Day of February, 2025

Coke Morgan Stewart
*Acting Director of the United States Patent and Trademark Office*

CERTIFICATE OF CORRECTION (continued)
U.S. Pat. No. 12,011,394 B2

Column 32, Line 45, delete "a" and insert --of a--

Column 33, Lines 21-34, delete "Whenever a........therebetween." and insert the same at Line 22, as a new paragraph